United States Patent
McNutt

(10) Patent No.: US 9,212,992 B2
(45) Date of Patent: Dec. 15, 2015

(54) APPARATUS AND METHOD FOR SENSING INCIDENT LIGHT HAVING DUAL PHOTODIODE TO ABSORB LIGHT IN RESPECTIVE DEPLETION REGIONS CONTROLLED BY DIFFERENT BIAS VOLTAGES

(71) Applicant: Microsemi Corporation, Aliso Viejo, CA (US)

(72) Inventor: Michael J. McNutt, Lake Forest, CA (US)

(73) Assignee: Microsemi Corporation, Aliso Viejo, CA (US)

( * ) Notice: Subject to any disclaimer, the term of this patent is extended or adjusted under 35 U.S.C. 154(b) by 253 days.

(21) Appl. No.: 13/943,305

(22) Filed: Jul. 16, 2013

(65) Prior Publication Data

US 2014/0021378 A1    Jan. 23, 2014

Related U.S. Application Data

(60) Provisional application No. 61/673,079, filed on Jul. 18, 2012.

(51) Int. Cl.
*H01L 31/00*    (2006.01)
*G01N 21/55*    (2014.01)
*H01L 31/02*    (2006.01)
(Continued)

(52) U.S. Cl.
CPC ............ *G01N 21/55* (2013.01); *H01L 27/1443* (2013.01); *H01L 27/14647* (2013.01); *H01L 31/02019* (2013.01); *H01L 31/103* (2013.01)

(58) Field of Classification Search
CPC ............ H01L 27/1461; H01L 27/1463; H01L 27/14621; H01L 31/105; H01L 27/14634; H01L 27/14667
USPC ........ 250/214.1, 214 R, 239, 208.1, 205, 226; 257/458–462, 290–292, 225, 252–257
See application file for complete search history.

(56) References Cited

U.S. PATENT DOCUMENTS 3,617,753 A   11/1971 Kato
4,011,016 A   3/1977 Layne
(Continued)

OTHER PUBLICATIONS

International Search Report for parallel application PCT/US2013/050810 by Korean Intellectual Property Office, mailed Oct. 15, 2013.
(Continued)

*Primary Examiner* — Que T Le
(74) *Attorney, Agent, or Firm* — Simon Kahn

(57) ABSTRACT

A solid-state photodetector with variable spectral response that can produce a narrow or wide response spectrum of incident light. Some embodiments include a solid-state device structure that includes a first photodiode and a second photodiode that share a common anode region. Bias voltages applied to the first photodiode and/or the second photodiode may be used to control the thicknesses of depletion regions of the photodiodes and/or a common anode region to vary the spectral response of the photodetector. Thickness of the depletion regions and/or the common anode region may be controlled based on resistance between multiple contacts of the common anode region and/or capacitance of the depletion regions. Embodiments include control circuits and methods for determining spectral characteristics of incident light using the variable spectral response photodetector.

18 Claims, 20 Drawing Sheets

(51) Int. Cl.
*H01L 31/103* (2006.01)
*H01L 27/144* (2006.01)
*H01L 27/146* (2006.01)

(56) References Cited

U.S. PATENT DOCUMENTS

| | | |
|---|---|---|
| 4,804,833 A | 2/1989 | Matsubara |
| 5,747,863 A | 5/1998 | Shoda |
| 5,999,271 A | 12/1999 | Shih |
| 6,359,324 B1 * | 3/2002 | Tichauer ............ 257/462 |
| 6,787,757 B2 | 9/2004 | Comeau |
| 7,601,981 B1 | 10/2009 | Moon |
| 2004/0178421 A1 | 9/2004 | Kuan |

OTHER PUBLICATIONS

Written Opinion of the International Searching Authority for parallel application PCT/US2013/050810 by Korean Intellectual Property Office, mailed Oct. 15, 2013.

\* cited by examiner

APPARATUS AND METHOD FOR SENSING INCIDENT LIGHT HAVING DUAL PHOTODIODE TO ABSORB LIGHT IN RESPECTIVE DEPLETION REGIONS CONTROLLED BY DIFFERENT BIAS VOLTAGES

CROSS REFERENCE

The present application claims priority under 35 U.S.C. §119 to U.S. Provisional Patent Application No. 61/673,079, entitled "SOLID-STATE PHOTODETECTOR WITH VARIABLE SPECTRAL RESPONSE," filed Jul. 18, 2012, the entire disclosure of which is incorporated herein by reference for all purposes.

BACKGROUND

1. Field

The present disclosure relates to light sensors in general and, in particular, to a solid-state photodetector with voltage variable spectral response.

2. Background

Light sensors or photodetectors have many applications in a variety of fields from scientific instruments to consumer electronics. Light sensors may be used to measure properties of light at particular wavelengths of interest or over a range of wavelengths. For example, a color analyzer may determine the color properties of incident light. Color analyzers may be used to compare color levels of materials or color reference of displays such as computer monitors or televisions.

Spectrometers measure the properties of light over a range of wavelengths of light. Spectrometers may be used for spectroscopy of a light source to determine spectral properties of the light source. Spectrometers may also be used in spectroscopy (e.g., Raman spectroscopy, infrared spectroscopy, etc.) to determine chemical or physical properties of an illuminated sample.

Many current light sensors use photodiodes that are sensitive to light in a range of frequencies. Particular light components (i.e., colors, frequencies, or ranges of frequencies of light) may be detected through the use of color filters or diffraction gratings. For example, a color analyzer may have three photodiodes with red, green, and blue color filters to isolate components of incident light. To sense light intensity across a range of wavelengths, spectrometers typically use optical prisms or diffraction gratings to separate light into component wavelengths and an array of photodiodes that detect the refracted or diffracted light to measure the spectral components.

SUMMARY

Various embodiments described herein are directed to a solid-state photodetector with variable spectral response. Some embodiments include a photodiode with a voltage variable depletion region thickness that can produce a narrow or a wide response spectrum anywhere in the long wave UV to shortwave infrared band. Some embodiments include a solid-state device structure that forms a first photodiode having a first depletion region proximate to a light acceptance surface of the photodetector and a second photodiode having a second depletion region, where the first depletion region is between the light acceptance surface and the second depletion region. The first depletion region and the second depletion region may be separated by a common anode region of the first and second photodiodes.

Bias voltages of the first photodiode and the second photodiode may determine the thicknesses of the depletion regions and the common anode region to vary the spectral response of the first photodiode based on absorption depth of incident light. In embodiments, thickness of the first depletion region of the first photodiode and the common anode region are controlled based on resistance measurements between multiple contacts of the common anode region. In embodiments, thickness of the depletion region of the first photodiode and the common anode region are controlled based on capacitance of the first photodiode depletion region and/or the second photodiode depletion region.

Measured photocurrent of the first photodiode may be processed at multiple voltage bias settings corresponding to various thicknesses of the first depletion region of the first photodiode to determine spectrally dependent photocurrent measurements for various ranges of incident light. Measured photocurrent of the second photodiode may be used to adjust measured photocurrent of the first photodiode to produce a desired response. The variable spectral response photodetector may be used in light sensing applications including human eye response sensors, color analyzers, spectrometers, and the like.

Some embodiments include an apparatus for sensing incident light that includes a light detector that receives the incident light at a light acceptance surface. The light detector may include a first photodiode that absorbs a first portion of the incident light in a first depletion region and generates a photocurrent responsive to the absorbed first portion of incident light. The light detector may include a second photodiode that absorbs a second portion of the incident light in a second depletion region. The first depletion region of the first photodiode may be between the second depletion region of the second photodiode and the light acceptance surface. The apparatus may include a detector driver module coupled with the light detector that is configured to apply a first bias voltage to the first photodiode, where a thickness of the first depletion region is controlled at least in part based on the first bias voltage, apply a second bias voltage different than the first bias voltage to the first photodiode, where the thickness of the first depletion region is controlled at least in part based on the second bias voltage, measure the photocurrent of the first photodiode at each of the first and second bias voltages to obtain a at least two photocurrent measurements, and determine a spectral component of the incident light based at least in part on the at least two photocurrent measurements.

In some embodiments the detector driver module may be configured to apply a third bias voltage to the second photodiode while applying the first bias voltage to the first photodiode, the thickness of the second depletion region controlled at least in part based on the third bias voltage, measure the photocurrent of the first photodiode at the third bias voltage, apply a fourth bias voltage to the second photodiode while applying the second bias voltage to the first photodiode, the fourth bias voltage different from the third bias voltage, the thickness of the second depletion region controlled at least in part based on the fourth bias voltage; and determine the spectral component of the incident light based at least in part on the photocurrent measurements at the third and fourth bias voltages. The third and fourth bias voltages may be selected such that a thickness of a common anode region between the first depletion region and the second depletion region is substantially the same when the first and second bias voltages are applied. The thickness of the common anode region may be controlled at least in part responsive to a resistance of the common anode region. The detector driver module may be configured to control the thickness of the first depletion region at each of the first and second bias voltages based at least in part on a capacitance of the first depletion region. The detector driver module may be configured to measure a photocurrent of the second photodiode responsive to the absorbed second portion of the incident light at one or more of the first and second bias voltages to obtain one or more backgate photocurrent measurements and determine a second spectral component of the incident light based at least in part on the at least two photocurrent measurements and the one or more backgate photocurrent measurements.

In some embodiments, the detector driver module includes a first voltage control module coupled with the first photodiode, a first current measurement module coupled with the first photodiode, and a processor module coupled with the first voltage control module and the first current measurement module, the processor module configured to determine the spectral component of the incident light based at least in part on the at least two photocurrent measurements via the first current measurement module and light absorption depth information. The detector driver module may include a second voltage control module coupled with the second photodiode and a second current measurement module coupled with the second photodiode, where the processor module is further coupled with the second voltage control module and the second current measurement module, and where the processor module may be further configured to determine the spectral component of the incident light based at least in part on photocurrent measurements via the second current measurement module at each of the first and second bias voltages.

Some embodiments include a method for sensing incident light received at a light acceptance surface that may include applying a first bias voltage to a first photodiode that absorbs a first portion of the incident light in a first depletion region between the light acceptance surface and a second depletion region of a second photodiode, the first photodiode generating a photocurrent responsive to the absorbed first portion of incident light, a thickness of the first depletion region controlled at least in part based on the first bias voltage, measuring the photocurrent of the first photodiode at the first bias voltage to obtain a first photocurrent measurement, applying a second bias voltage to the first photodiode, the thickness of the first depletion region controlled at least in part based on the second bias voltage, measuring the photocurrent of the first photodiode at the second bias voltage to obtain a second photocurrent measurement, and determining a spectral component of the incident light based at least in part on the first photocurrent measurement and the second photocurrent measurement.

In some embodiments, the method includes applying a third bias voltage to the second photodiode while applying the first bias voltage to the first photodiode, a thickness of the second depletion region controlled at least in part based on the third bias voltage, measuring the photocurrent of the first photodiode at the third bias voltage to obtain a third photocurrent measurement, applying a fourth bias voltage to the second photodiode while applying the second bias voltage to the first photodiode, the fourth bias voltage different from the third bias voltage, the thickness of the second depletion region controlled at least in part based on the fourth bias voltage, and determining the spectral component of the incident light further based at least in part on the third photocurrent measurement and the fourth photocurrent measurement. Applying the third and fourth bias voltages may include controlling a thickness of a common anode region between the first depletion region and the second depletion region to be substantially equal when the first and second bias voltages are applied. The thickness of the common anode region may be controlled at least in part responsive to a resistance of the common anode region. Applying the first and second bias voltages may include controlling the thickness of the first depletion region at each of the first and second bias voltages based at least in part on a capacitance of the first depletion region.

In some embodiments, the method includes measuring a backgate photocurrent responsive to a second portion of the incident light absorbed in the second depletion region of the second photodiode at one or more of said first and second bias voltages and determining a second spectral component of the incident light based at least in part on at least one of the first and second photocurrent measurements and the one or more backgate photocurrent measurements. Determining the second spectral component may include subtracting a portion of the one or more backgate photocurrent measurements from the at least one of the first and second photocurrent measurements, the portion of the one or more backgate photocurrent measurements subtracted from the at least one of the first and second photocurrent measurements based at least in part on the first bias voltage.

In some embodiments, the method includes measuring photocurrent at a first plurality of bias points. The measurements at the first plurality of bias points may be made by iteratively stepping the thickness of the first depletion region by a predetermined step thickness by, at least in part, modifying the second bias voltage and measuring the photocurrent of the first photodiode. The method may include determining an amount of received light at a second plurality of wavelength ranges by solving a matrix calculation based at least in part on the measured photocurrent at the first plurality of bias points and light absorption depth information. The number of photocurrent measurements measured at the first plurality of bias points may be greater than the number of wavelength ranges of the second plurality of wavelength regions. The method may include adjusting the matrix calculation to adjust a calculated spectral response based at least in part on a metric of the measured photocurrent at one or more bias points. The metric of the measured photocurrent may include a combined incident light level.

Some embodiments include a photodetector that includes a first photodiode that absorbs a first portion of incident light in a first depletion region, the first photodiode generating a photocurrent responsive to the absorbed first portion of incident light and a second photodiode that absorbs a second portion of the incident light in a second depletion region, the absorbed second portion including a portion of the incident light not including the first portion of the incident light. Spectral response of the photocurrent may be controlled based at least in part on a first bias voltage applied between a first cathode contact coupled with a first cathode region of the first photodiode and a common anode contact coupled with a common anode region of the first photodiode and the second photodiode. The thickness of the first depletion region may be controlled at least in part by the first bias voltage and a second bias voltage applied between the common anode contact and a second cathode contact coupled with a second cathode region of the second photodiode. The common anode contact may include a first common anode contact coupled with the common anode region and a second common anode contact coupled with the common anode region, wherein a resistance between the first common anode contact and the second common anode contact depends at least in part on a thickness of the common anode region. The photodetector may include a semiconductor substrate layer comprising the first depletion region and a transparent gate electrode in between a light reception portion of the photodetector that receives the incident light and the first depletion region, wherein the transparent gate electrode is biased to form the first cathode region of the first photodiode between the first depletion region and the transparent gate electrode.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label. The drawing figures are not necessarily drawn to scale and certain figures may be shown in exaggerated or generalized form in the interest of clarity and conciseness.

DETAILED DESCRIPTION OF THE INVENTION

Figure 1A:
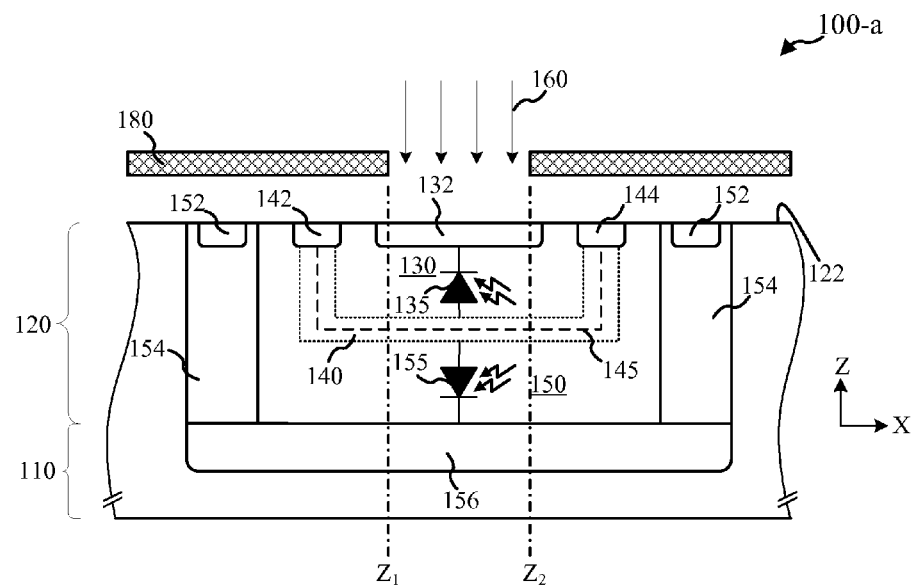
FIG. 1A illustrates a cross-section of a solid-state photodetector with variable spectral response in accordance with various embodiments.

Embodiments of the present disclosure are directed to a solid-state photodetector with variable spectral response. Some embodiments include a photodiode with a voltage variable photocurrent collection boundary that can produce a narrow or a wide response spectrum anywhere in the long wave UV to shortwave infrared band. Some embodiments include a solid-state device structure that forms a first photodiode having a first depletion region proximate to a light acceptance surface of the photodetector and a second photodiode having a second depletion region opposite of a common anode region from the light acceptance surface.

Bias voltages of the first photodiode and the second photodiode may determine the thicknesses of the depletion regions and the common anode region to vary the spectral response of the first photodiode based on absorption depth of incident light. In embodiments, the thickness of the common anode region may be controlled to be relatively thin to accurately control the depth of the photocurrent collection boundary between the first photodiode depletion region and the second photodiode depletion region. In embodiments, thicknesses of the first photodiode depletion region and the second photodiode depletion region are controlled based on resistance measurements between multiple contacts of the common anode region. In embodiments, thicknesses of the first photodiode depletion region and the second photodiode depletion region are controlled based on capacitance of the first photodiode depletion region and/or the second photodiode depletion region.

Measured photocurrent of the first photodiode may be processed at multiple voltage bias settings corresponding to various thicknesses of the first depletion region of the first photodiode to determine spectrally dependent photocurrent measurements for various ranges of incident light. Measured photocurrent of the second photodiode may be used to adjust measured photocurrent of the first photodiode to produce a desired response. The variable spectral response photodetector may be used in light sensing applications including human eye response sensors, color analyzers, spectrometers, and the like.

This description provides examples, and is not intended to limit the scope, applicability or configuration of the invention. Rather, the ensuing description will provide those skilled in the art with an enabling description for implementing embodiments of the invention. Various changes may be made in the function and arrangement of elements.

Thus, various embodiments may omit, substitute, or add various procedures or components as appropriate. For instance, it should be appreciated that the methods may be performed in an order different than that described, and that various steps may be added, omitted or combined. Also, aspects and elements described with respect to certain embodiments may be combined in various other embodiments. It should also be appreciated that the following systems, methods, devices, and software may individually or collectively be components of a larger system, wherein other procedures may take precedence over or otherwise modify their application.

FIG. 1A illustrates a cross-section of a solid-state photodetector 100-a with variable spectral response in accordance with various embodiments. In embodiments, variable spectral response photodetector 100-a includes various layers and/or regions doped to have the described electrical properties including excess of negative charge carriers (N-type) or positive charge carriers (P-type), as is known in the art. Variable spectral response photodetector 100-a may have a two-layer structure such as the structure illustrated in FIG. 1A including a P–substrate 110 and P–epitaxial layer 120. In the two-layer structure illustrated in FIG. 1A, P–substrate 110 may include N+ buried implant layer 156. The structure of variable spectral response photodetector 100-a may further include N-well 154, N+ implant region 152, P+ implant regions 142 and/or 144, and N+ implant region 132 in P–epitaxial layer 120.

For the convenience of description in the figures, a z-axis may be defined as an axis orthogonal to substrate layers of the photodetector, while an x-axis and y-axis may define a plane parallel to a surface of substrate layers of the photodetector. Also, for description purposes, a negative direction and a positive direction along the x-axis may be referred to as a left direction and a right direction, respectively, a negative direction and a positive direction along the y-axis may be referred to as a front direction and a rear direction, respectively, and a negative direction and a positive direction along the z-axis may be referred to as a lower direction and an upper direction, respectively. In the ensuing description, various elements may be described by their relative positions based on the defined axes in the figures and these identifiers should not be construed to define absolute positional requirements of the photodetector or the various elements.

Generally, the various regions of variable spectral response photodetector 100-a may form a top photodiode 135 and a bottom or backgate photodiode 155 that share a common anode region 140. The top photodiode 135 may be electrically contacted through P+ implant regions 142 and/or 144 (coupled to common anode region 140) and N+ implant region 132 (cathode). The bottom photodiode 155 may be electrically contacted through P+ implant regions 142 and/or 144 (coupled to common anode region 140) and N+ implant region 152 (coupled to N+ buried implant layer 156 through N-Well 154). Coupling of electrical circuits to the various implant regions may be accomplished through the use of known semiconductor processing steps (contacts, interconnect, wire bonding, etc.). Reference to a contact associated with one of the various implant regions assumes such electrical coupling as is known in the art.

Generally, the ensuing description uses the example of a two-layer structure with P– substrate 110 and P–epitaxial layer 120, however, other single-layer or multi-layer configurations, layer growth, deposition, or implant techniques may be used to form a variable spectral response photodetector according to various embodiments. For example, a variable spectral response photodetector may be constructed using a single-layer or multi-layer configuration with N-type semiconductor layers. The constituent semiconductor materials may be any of various suitable semiconductor materials for photodetector applications such as germanium, gallium arsenide, indium gallium arsenide, indium phosphide, sapphire, and the like.

When a reverse bias voltage is applied to top photodiode 135, depletion region 130 may form between the N+ implant or cathode region 132 and the common anode region 140. When a reverse bias voltage is applied to bottom photodiode 155, depletion region 150 may form between the common anode region 140 and the N+ buried implant layer or backgate cathode region 156. The depth and thickness of the depletion region 130, the depletion region 150, and the common anode region 140 may vary based on the bias voltages applied to the top photodiode 135 and the bottom photodiode 155.

Generally, a variable spectral response photodetector 100 may be arranged to accept incident light from a light source or object. In the embodiment illustrated in FIG. 1A, incident light 160 is received by the variable spectral response photodetector 100-a at the silicon surface 122. Variable spectral response photodetector 100 may have a metal layer 180 that shields regions other than a portion of the semiconductor surface 122 that is intended to receive the incident light 160, which advantageously may prevent edge complications from regions bordering top photodiode 135 and bottom photodiode 155. As the incident light 160 passes through the semiconductor layers of variable spectral response photodetector 100, photons from the incident light 160 are absorbed and generate photocurrent in top photodiode 135 and/or bottom photodiode 155.

In some configurations, reference to various characteristics of depletion region 130, common anode region 140, and/or depletion region 150 may refer to the portions of these regions in the photo-active portion of variable spectral response photodetector 100. For example, the photo-active portion of variable spectral response photodetector 100-a may be illustrated in FIG. 1A as the portion bounded by axis lines $Z_1$ and $Z_2$ that generally receives incident light 160. Accordingly, reference to characteristics of top photodiode 135, depletion region 130, common anode region 140, bottom photodiode 155, and/or depletion region 150, should not be construed to require that the characteristic holds for the entirety of the device and/or region. For example, depletion region 130 may generally be described as in between depletion region 150 and the semiconductor surface 122. It should be understood that this characteristic may refer to the photo-active portions of these respective regions.

Absorption depth of incident light in semiconductor materials varies by wavelength. Generally, shorter wavelength light is absorbed at shallower depths and longer wavelength light has a deeper absorption depth. In silicon for example, blue light with a wavelength of 450 nm may have an absorption depth, defined as a light intensity of 1/e (36%) of its original value, of approximately 0.3 μm, while green light having a wavelength of approximately 530 nm may have an absorption depth of approximately 1.0 µm, and red light having a wavelength of approximately 700 nm may have an absorption depth of approximately 4.0 p.m. Other semiconductor materials have similar absorption properties, with absorption depths varying in the range of sub-micron depths to more than a centimeter for infra-red wavelengths in some semiconductor materials. In the present description, a silicon photodetector is described for optical responses in the visible range and infra-red regions, however, it should be understood that an appropriate semiconductor may be selected for a particular application based on a desired range of spectral response and material thickness.

Photons absorbed in the depletion region 130 of the top photodiode 135 produce electron-hole pairs as part of the absorption process, i.e. the energy of the photon separates a negatively charged electron from the silicon crystal structure making it a free carrier and leaving a positively charged hole in the structure. Described in terms of energy, an electron in the silicon valence band absorbs the photon energy and crosses the silicon bandgap to the conduction band, leaving behind a free hole. The free electron is separated from the hole by the relatively high electric field in the depletion region 130 and is collected at the cathode region 132. Similarly, an electron photocurrent is generated in the depletion region 150 of bottom photodiode 155 and is collected at the backgate cathode region 156. The two hole currents are combined and collected by the common anode region 140. In some embodiments, the photocurrent at the common anode region may be ignored since it contains less information than the separate cathode photocurrents of the photodiodes 135 and 155, respectively.

In the common anode region 140, approximately half of the electrons generated by absorbed photons in the common anode region 140 may diffuse to the depletion region 130, and the remaining electrons may diffuse to the depletion region 150. In some embodiments, the photodiodes 135 and 155 are biased to form a relatively thin common anode region 140, in which case common anode region 140 may be modeled as a collection boundary 145 between depletion region 130 and depletion region 150. Thus, a narrow depletion region 140 may provide more accurate control of the spectral response of photodetector 100 because the exact location of the boundary between common anode region 140 and depletion regions 130 and/or 150 need not be determined Control of the thickness of common anode region 140 may be used to accurately adjust the depth of collection boundary 145, as will be discussed in more detail below.

Because absorption depth varies with wavelength of incident light, spectral response of the top photodiode 135 may be controlled by varying the thickness of the depletion region 130, particularly by adjusting the depth of the collection boundary 145 relative to the semiconductor surface 122. For example, a relatively small reverse bias voltage applied to photodiode 135, combined with a relatively larger reverse bias voltage applied to photodiode 155 may produce a thin depletion region 130 that is close to the semiconductor surface and/or cathode region 132. With this relatively thin depletion region 130, light having shorter wavelengths such as blue light may be absorbed in depletion region 130 while longer wavelength light passes through depletion region 130 without being absorbed. The longer wavelength light may be absorbed in the depletion region 150 of the photodiode 155. Increasing the reverse bias voltage applied to photodiode 135 may generally increase the thickness of the depletion region 130. Similarly, thicknesses of the common anode region 140 and/or depletion region 150 may be controlled by varying the reverse bias voltage applied to photodiode 135 in conjunction with a reverse bias voltage applied to the bottom photodiode 155.

In certain embodiments, common anode region 140 may be contacted via two common anode contacts. For example, common anode region 140 may be coupled with a first P+ implant region 142 and a second P+ implant region 144 on opposite sides of the N+ implant cathode region 132. The first and second P+ implant regions 142, 144 may be used to determine thickness of the common anode region 140 based on a resistance measurement between the P+ implant regions 142, 144 as described in more detail below. However, some embodiments have a single P+ implant region or multiple P+ implant regions that are electrically coupled in the variable spectral response photodetector 100.

The electrical structure of variable spectral response photodetector 100 may include two photodiodes 135 and 155 sharing a common anode region that varies in depth, and optionally in thickness, based on bias voltages applied to the two photodiodes 135 and 155. FIG. 1A illustrates a vertical structure for variable spectral response photodetector 100-*a* where depletion region 130 of the top photodiode 135 is formed proximate to the surface 122 of the variable spectral response photodetector 100-*a* and between cathode region 132 and common anode region 140. In the vertical structure of FIG. 1A, depletion region 150 of photodiode 155 is formed between common anode region 140 and buried N+ cathode region 156. However, other structures are possible for variable spectral response photodetector 100 including horizontal photodiode structures. For example, depletion regions 130 and 150 and common anode region 140 may be formed as vertical layers and incident light 160 may be received by the light detector from a horizontal direction at a vertical plane proximate to depletion region 130.

Figure 1B:
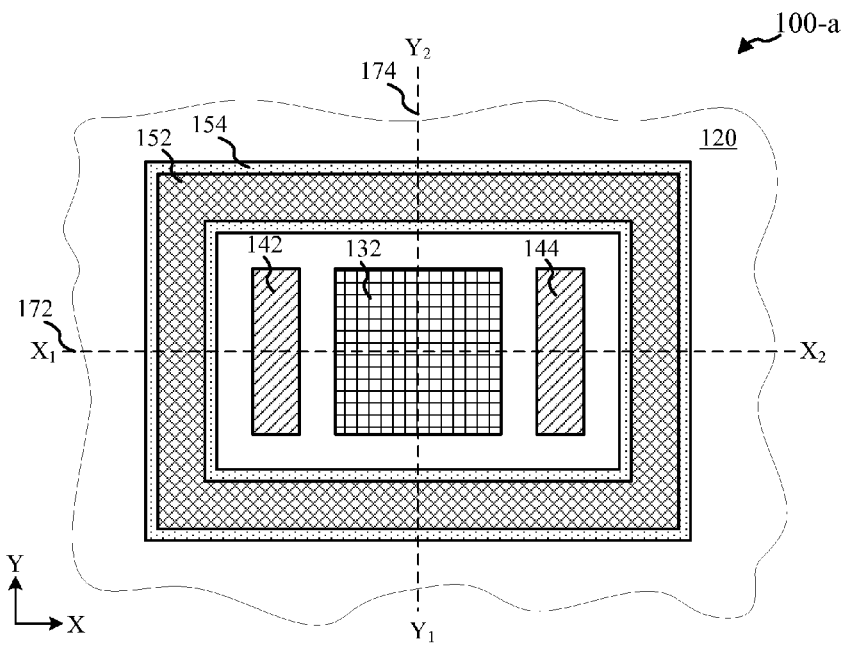
FIG. 1B shows a top or plan view of a solid-state photodetector with variable spectral response in accordance with various embodiments.

FIG. 1B shows a top or plan view of variable spectral response photodetector 100-*a* in accordance with various embodiments. Cross-sectional planes may be defined to assist in illustrating cross sections of variable spectral response photodetector 100-*a*. For example, a cross-sectional plane $X_1$-$X_2$ 172 may be described as a left-to-right cross-section and a cross-sectional plane $Y_1$-$Y_2$ 174 may be described as a front-to-back cross section of variable spectral response photodetector 100-*a*. For clarity, light shield layer 180 is not illustrated in FIG. 1B and may be omitted in subsequent figures of various embodiments.

As seen in the plan view, FIG. 1B illustrates that N-Well region 154 may surround N+ cathode region 132 and P+ common anode regions 142 and 144. N-Well region 154 may include one or more N+ implant regions 152. FIGS. 1A and 1B illustrate only one example of possible structures for variable spectral response photodetector 100-*a* and other topographies and/or layouts are within the scope of the present disclosure and will be readily recognized by one of skill in the art.

As described above, the spectral response of top photodiode 135 and bottom photodiode 155 may depend on respective thicknesses of depletion region 130 and depletion region 150, which may be defined by a depth of the collection boundary 145 between the depletion regions. For example, a relatively thin depletion region 130 may result in a spectral response of the top photodiode 135 having primarily shorter wavelength components and fewer longer wavelength components. In this instance, longer wavelength components not absorbed by the top photodiode 135 may be absorbed by the bottom photodiode 155, resulting in a primarily longer-wavelength spectral response of the bottom photodiode 155. Biasing top photodiode 135 and bottom photodiode 155 to have a relatively thicker depletion region 130 may result in more longer wavelengths absorbed by top photodiode 135.

Figure 2A:
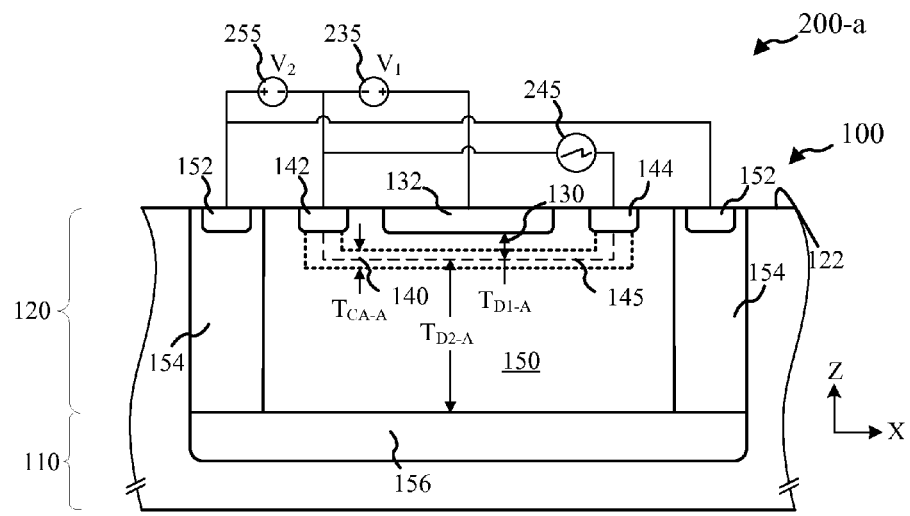
FIG. 2A illustrates a first control state for a light detector device employing a variable spectral response photodetector in accordance with various embodiments.
Figure 2B:
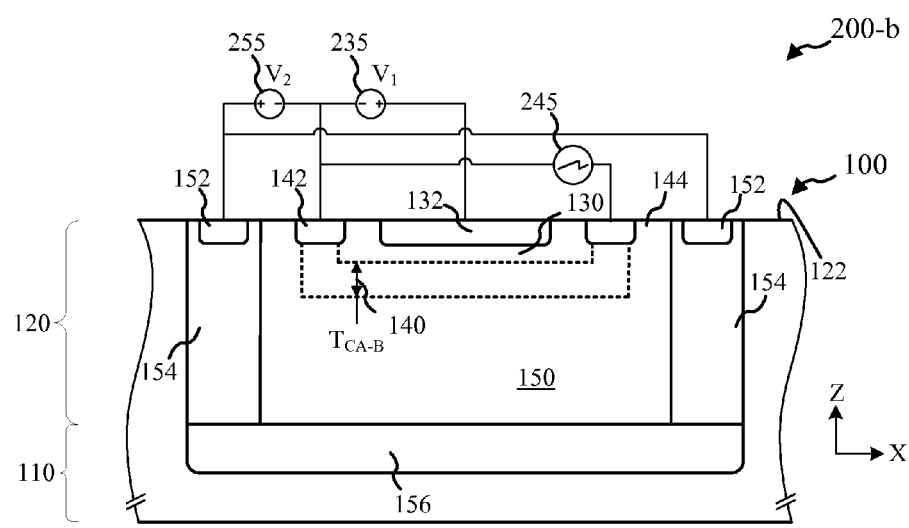
FIG. 2B illustrates a second control state for a light detector device employing a variable spectral response photodetector in accordance with various embodiments.
Figure 2C:
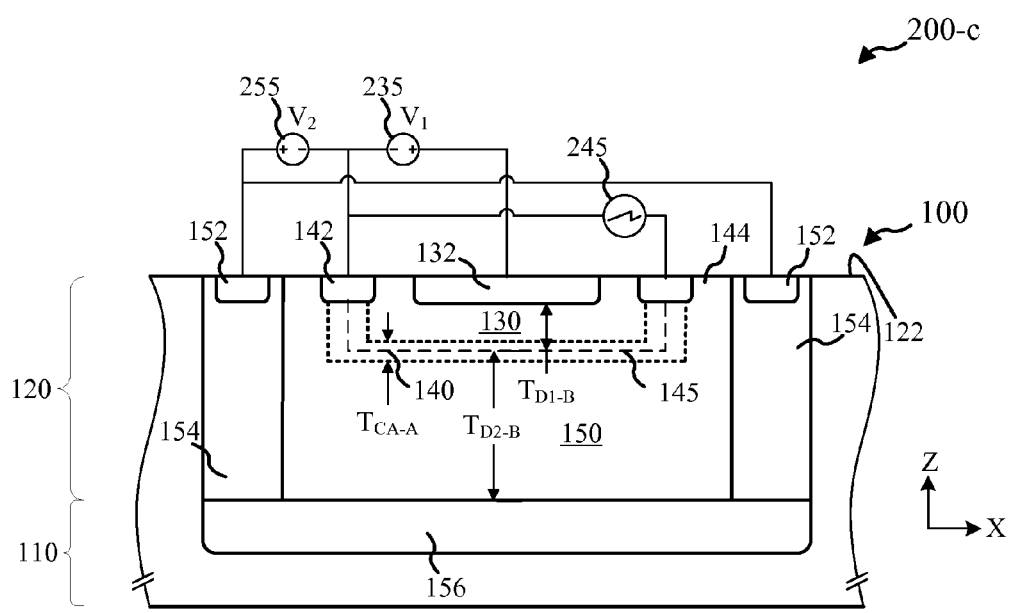
FIG. 2C illustrates a third control state for a light detector device employing a variable spectral response photodetector in accordance with various embodiments.

As mentioned above, aspects of various embodiments are directed to accurately controlling spectral response and/or calibration of an apparatus or system employing a variable spectral response photodetector according to the present disclosure. Referring generally to FIGS. 2A, 2B, and 2C, control and/or calibration of spectral response of variable spectral response photodetector 100 using resistance measurement of the common anode region is described in more detail, according to various embodiments. As illustrated in FIGS. 2A, 2B, and 2C, a system employing variable spectral response photodetector 100 may include controllable voltage source 235 for applying a bias voltage between N+ cathode region 132 and P+ implant regions 142 and 144, controllable voltage source 255 for applying a bias voltage between N+ cathode region 152 and P+ implant regions 142 and 144, and resistance measurement unit 245 for measuring a resistance between P+ implant regions 142 and 144. While not illustrated specifically in FIGS. 2A, 2B, and 2C, the present description will continue to refer to the top photodiode 135 and bottom or backgate photodiode 155 as illustrated schematically in FIG. 1A.

FIG. 2A illustrates a first control state 200-a for a light detector device employing a variable spectral response photodetector 100 in accordance with various embodiments. To establish the first control state 200-a, a first voltage may be applied to the top photodiode 135 by voltage source 235. For example, a relatively small reverse bias voltage or a voltage of zero volts may be applied by voltage source 235. Initially, voltage source 255 may also be set to a relatively small voltage or zero volts. Because the top photodiode 135 has a relatively small reverse bias, the effective thickness $T_{D1-A}$ of depletion region 130 may be relatively thin. Voltage source 255 may then be increased until a desired thickness $T_{CA-A}$ of common anode region 140 is established. Thickness of common anode region 140 may be determined by measuring resistance between P+ implant regions 142 and 144. For example, if the resistivity of the P-epitaxial layer is 10 Ω-cm, the resistance of a 0.1 μm thick common anode region 140 may be 1 MΩ. Resistance between P+ implant regions 142 and 144 may be measured, for example, by applying a small (e.g., 0.1 volt) voltage differential between contacts of P+ implant regions 142 and 144 and measuring current flow between the respective contacts.

First control state 200-a may correspond to a first measurement state for variable spectral response photodetector 100. In embodiments, thickness $T_{XA-A}$ of the common anode region 140 for measurement states is selected to be relatively thin to reduce the amount of absorbed light within the common anode region 140 and provide improved control of the depth of collection boundary 145. For example, thickness $T_{CA-A}$ of the common anode region 140 for measurement states may be approximately 0.1 μm. The actual depth of collection boundary 145 below the semiconductor surface 122 may be determined by the depth of N+ cathode region 132 and the thickness $T_{D-D4}$ of depletion region 130. In the first control state 200-a, depletion region 150 has a thickness of $T_{D2-A}$ extending from the collection boundary 145 to N+ buried cathode 156. Electron photocurrent generated in depletion region 130 for variable spectral response photodetector 100 in first control state 200-a may be measured at voltage source 235. Electron photocurrent generated in depletion region 150 for the first control state 200-a may be measured at voltage source 255. Photodiode current may be measured at voltage sources 235 and 255 using known circuit techniques (e.g., transimpedance amplifiers, etc.).

FIG. 2B illustrates a second control state 200-b for a light detector device employing a variable spectral response photodetector 100 in accordance with various embodiments. Starting from the first control state 200-a, the reverse bias voltage applied by voltage source 255 may be decreased until the thickness of common anode region 140 increases by a desired step size. For example, for a step of 0.1 μm in depth of the collection boundary 145, the thickness of the common anode region 140 may be increased from 0.1 μm (e.g., $T_{CA-A}$) to 0.2 μm by lowering the voltage applied by voltage source 255 until the resistance between common anode contacts 142 and 144 decreases from 1.0 MΩ to 0.5 MΩ.

FIG. 2C illustrates a third control state 200-c for a light detector device employing a variable spectral response photodetector 100 in accordance with various embodiments. Third control state 200-c may correspond to a second measurement state for variable spectral response photodetector 100. Starting from the second control state 200-b, the reverse bias voltage applied by voltage source 235 may be increased until the thickness of the common anode region 140 decreases to again be substantially equal to thickness $T_{CA-A}$. For example, the reverse bias applied by voltage source 235 may be increased from control state 200-b until the resistance between common anode contacts 142 and 144 increases from 0.5 MΩ to 1.0 MΩ. In the third control state 200-c, the thickness $T_{D1-B}$ of depletion region 130 may be increased by substantially the desired step size from the thickness $T_{D1-A}$ of depletion region 130 in first control state 200-a, while the thickness $T_{D2-B}$ of depletion region 150 may decrease by substantially the desired step size from the thickness $T_{D2-A}$ of depletion region 150 in first control state 200-a.

Starting from the third control state 200-c, the steps described related to the second and third control states may be repeated to step the depth of the collection boundary 145 between the depletion region 130 of the top photodiode 135 and the depletion region 150 of the bottom photodiode 150 in controlled increments. Measurements of electron photocurrent of the top photodiode 135 and optionally of the bottom photodiode 155 may be made at each iteration of the third control state (e.g., with the thickness of the common anode region equal to $T_{CA-A}$). As the thickness of the depletion region 130 of the top photodiode 135 is increased, the depletion region 130 absorbs more wavelengths of light and receives additional photocurrent contribution from the absorbed light. Therefore, this procedure may be used to control the spectral response of the photodetector 100 by accurately controlling the thicknesses of the depletion region 130 of the top photodiode 135, the common anode region 140, and the depletion region 150 of the bottom photodiode 155. It is to be noted that increasing the thickness of the depletion region 130 of the top photodiode 135 while maintaining the thickness of the common anode region equal to a predetermined value, i.e. $T_{CA-A}$, results in a corresponding decrease in thickness of the depletion region 150 of the bottom photodiode 155. As the depletion region 150 is reduced in thickness it may absorb fewer wavelengths of light and thus receive less photocurrent contribution from the absorbed light. Conversely, decreasing the thickness of the depletion region 130 of the top photodiode 135 while maintaining the thickness of the common anode region equal to a predetermined value, i.e. $T_{CA-A}$, results in a corresponding increase in thickness of the depletion region 150 of the bottom photodiode 150. As the depletion region 150 is increased in thickness it may absorb more wavelengths of light and thus receive more photocurrent contribution from the absorbed light.

In some embodiments, capacitance of depletion region 130 and/or depletion region 150 may be used to control the spectral response of the photodetector 100 instead of or in addition to common anode region resistance. Capacitance of a diode depletion region generally decreases with increasing depletion region thickness. Using this known relationship, measured capacitance of the top photodiode 135 and bottom photodiode 155 may be used to determine thicknesses of depletion region 130, common anode region 140, and/or depletion region 150.

In some embodiments, the described procedures for setting the depth of collection boundary 145 based on common anode region resistance and/or depletion region capacitance may be used during an operational mode (e.g., before performing each measurement) of the variable spectral response photodetector 100 to sense light intensity across different ranges of wavelengths. In some embodiments, the described procedures are used for calibration of variable spectral response photodetector 100. For example, the procedures described above for setting the depth of collection boundary 145 and/or thicknesses of depletion region 130 and depletion region 150 may be used, and the calibrated drive voltages for the top and bottom photodiodes at various thicknesses of depletion regions 130 and 150 and/or depths of the collection boundary 145 may be stored in memory or non-volatile storage. The stored values may then be used in operation of the variable spectral response photodetector 100. Variable spectral response photodetectors 100 may be individually calibrated using the described procedures to reduce or eliminate response variations due to manufacturing process tolerances. Alternatively, calibration may be performed periodically or before each set of measurements based on the procedures for setting the depth of the collection boundary 145 and/or thicknesses of depletion regions 130 and/or 150 as described above.

Figure 3:
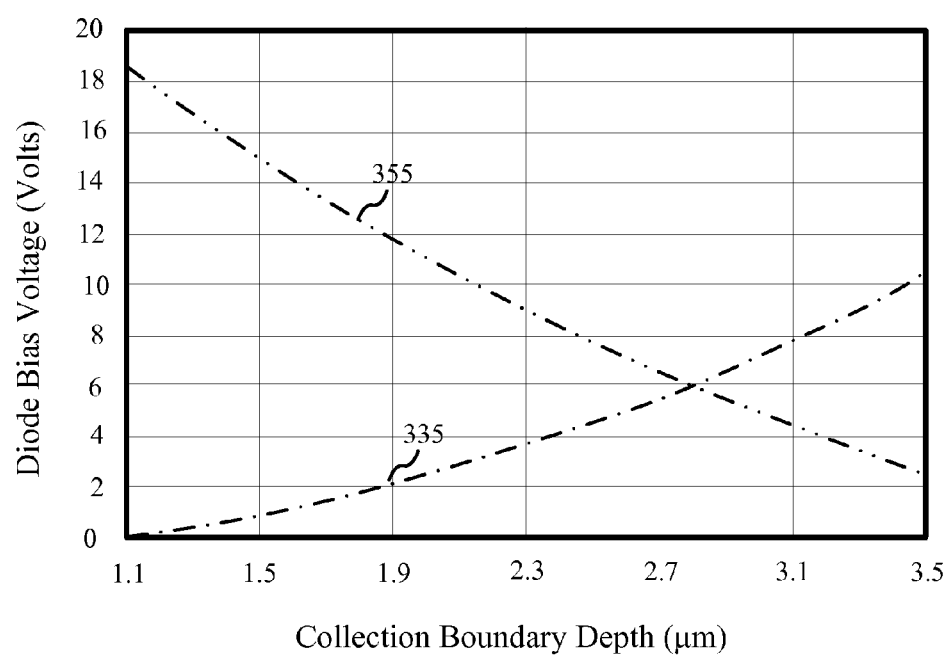
FIG. 3 illustrates example voltage settings for top and bottom photodiodes of a variable spectral response photodetector in accordance with various embodiments.

FIG. 3 illustrates example voltage settings for the top and bottom photodiodes with a consistent (e.g., 0.1 µm) common anode region thickness for various depths of the collection boundary 145, where the x-axis represents the depth of the collection boundary 145 and the y-axis represent the respective photodiode reverse bias in volts. Curves 335 and 355 illustrate the respective reverse bias voltages of the top photodiode 135 and bottom photodiode 155 that may be used to set a particular collection boundary depth, at a predetermined thickness of the common anode region 140, for an example variable spectral response photodetector 100. FIG. 3 illustrates that a voltage range of about 20V may be sufficient to provide a sufficient range of collection boundary depths for many visible light applications using a silicon substrate.

From the photocurrent measurements at various depths of the collection boundary 145, the amount of light absorbed from various wavelengths can be determined. The generated photocurrent of the top photodiode at a depth of the collection boundary, d, may be given by:

$$I_{td} = \sum_{k=0}^{n} A_k (1 - e^{(-d/\alpha_k)})$$

Where $A_k$ is the unknown incident light power at a wavelength k; $\alpha_k$ is the absorption depth of wavelength $\lambda_k$ for the constituent material; and d is defined as the distance from semiconductor surface 122 to the collection boundary 145. The generated photocurrent of the bottom or backgate photodiode 155 at a collection boundary depth, d, may be given by:

$$I_{bd} = \sum_{k=0}^{n} A_k \cdot e^{(-d/\alpha_k)}$$

To determine the incident light power at a specific wavelength or over a range of wavelengths, the electron photocurrent response of the top photodiode 135 and/or bottom photodiode 155 may be measured at multiple collection boundary depths and the values of $A_k$ may be calculated by matrix calculation. The calculated values of $A_k$ may include multiplying factors for surface reflectance and quantum efficiency. These factors may be accounted for by known techniques to determine the incident light amplitude for the various spectral components. Spectral response data including incident light power at N wavelengths (or wavelength ranges) may be generated by measuring electron photocurrent response at a number M thicknesses of the depletion region of the top photodiode, where M≥N.

Because shorter wavelength light may be absorbed in regions relatively close to the surface of the variable spectral response photodetector 100, resolution of shorter wavelength light may be limited by the thickness of the N+ cathode region 132. In some embodiments, the thickness of N+ cathode region 132 may be reduced to improve spectral resolution at shorter wavelengths. In some embodiments, resolution of the variable spectral response photodetector at shorter wavelengths may be improved through the use of various alternative cathode structures for the top photodiode 135.

Figure 4A:
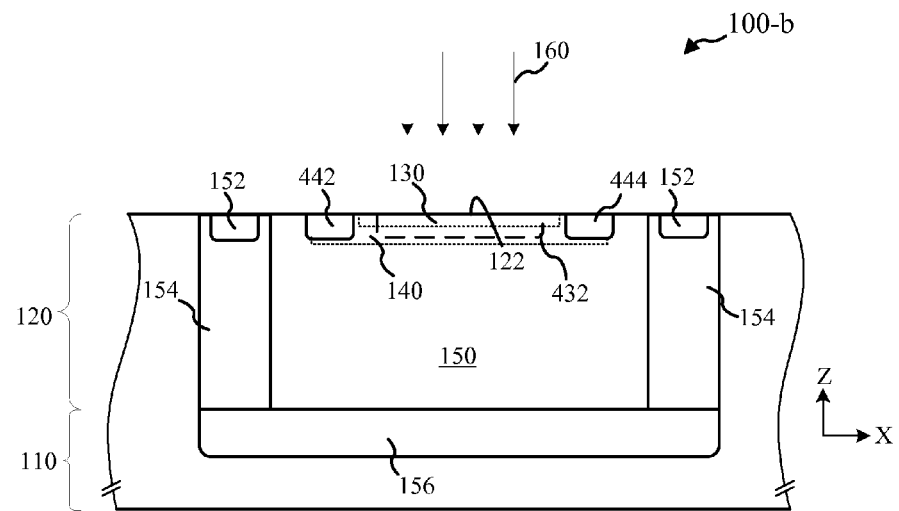
FIG. 4A illustrates a cross-section of a solid-state photodetector with variable spectral response in accordance with various embodiments.
Figure 4B:
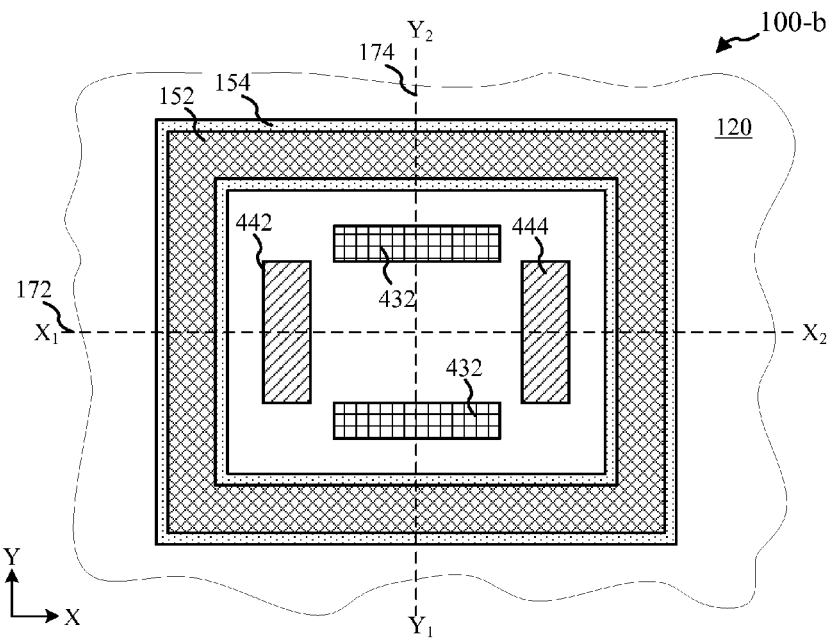
FIG. 4B shows a top or plan view of a solid-state photodetector with variable spectral response in accordance with various embodiments.

FIGS. 4A and 4B illustrate a variable spectral response photodetector 100-b with an alternative cathode structure for the top photodiode 135 in accordance with various embodiments. FIG. 4B illustrates a plan view of variable spectral response photodetector 100-b with left-to-right cross-sectional plane $X_1$-$X_2$ 172 and front to back cross-sectional plane Y1-Y2 174 illustrated for reference. FIG. 4A may illustrate a cross section of variable spectral response photodetector 100-b in cross-sectional plane $X_1$-$X_2$ 172.

Similarly to photodetector 100-a, variable spectral response photodetector 100-b may have a two-layer structure with a P−substrate 110 and P−epitaxial layer 120. N+ buried cathode 456 may be formed in P−substrate 110 and connected to N+ implant region 152 through N-Well 154 to form, generally, the cathode region of the bottom photodiode 155. The P−epitaxial layer 120 may have an inversion region close to the surface 122, which may form a thin (e.g., approximately 0.01 µm) N+ cathode region between N+ cathode implant regions 432 for top photodiode 135. P+ anode regions 442 and 444 may provide anode connections to the top photodiode 135 and bottom photodiode 155. FIG. 4A illustrates that the top photodiode 135 and bottom photodiode 155 can be biased such that the common anode region 140 is closer to the semiconductor surface 422 than may be possible with the N+ cathode implant region of the variable spectral response photodetector 100-a illustrated in FIGS. 1A and 1B.

Figure 5A:
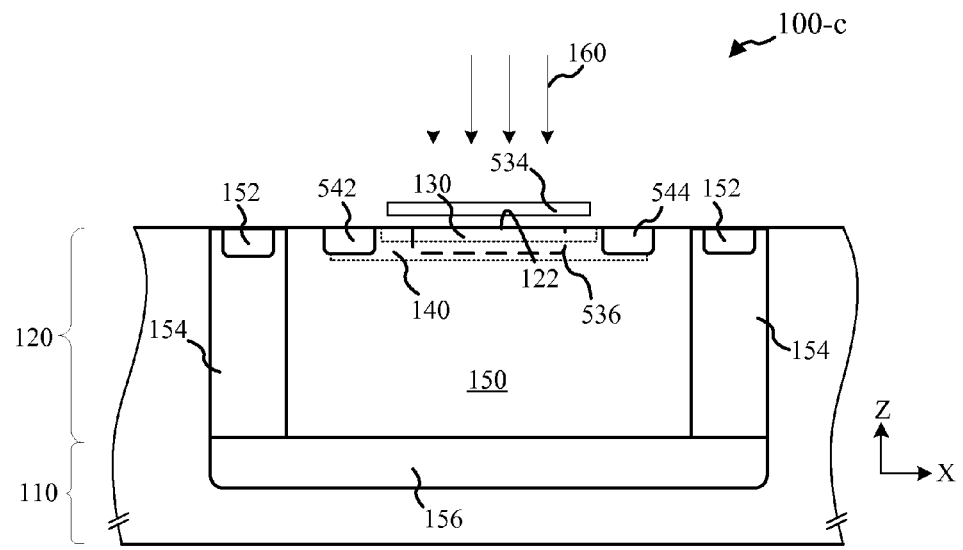
FIG. 5A illustrates a cross section of a photodetector employing a MOS photodiode cathode structure in accordance with various embodiments.
Figure 5B:
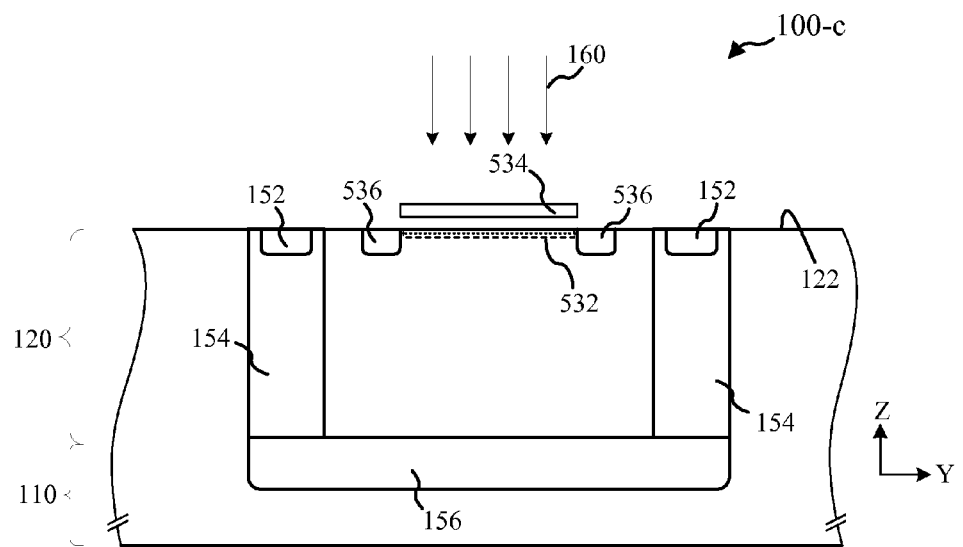
FIG. 5B illustrates a cross section of a photodetector employing a MOS photodiode cathode structure in accordance with various embodiments.
Figure 5C:
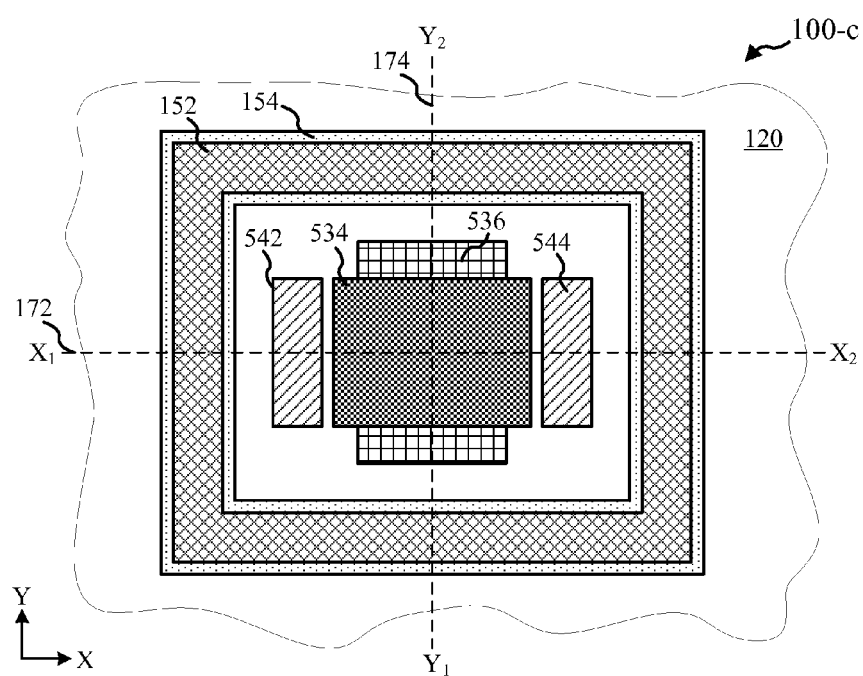
FIG. 5C illustrates a plan view of a photodetector employing a MOS photodiode cathode structure in accordance with various embodiments.

FIGS. 5A, 5B and 5C illustrate a variable spectral response photodetector 100-c employing a metal oxide semiconductor (MOS) cathode structure in accordance with various embodiments. FIG. 5C may illustrate a plan view of variable spectral response photodetector 100-c with left-to-right cross-sectional plane $X_1$-$X_2$ 172 and front to back cross-sectional plane $Y_1$-$Y_2$ 174 illustrated for reference. FIG. 5A may illustrate a cross section of variable spectral response photodetector 100-c in plane cross-sectional plane $X_1$-$X_2$ 172. FIG. 5B may illustrate a cross section of variable spectral response photodetector 100-c in plane cross-sectional plane $Y_1$-$Y_2$ 174.

Similarly to photodetectors 100-a and 100-b, variable spectral response photodetector 100-c may have a two-layer structure with a P–substrate 110 and P–epitaxial layer 120. N+ buried cathode 156 may be formed in P–substrate 110 and connected to N+ implant region 152 through N-Well 154 to form, generally, the cathode region of the bottom photodiode 155. Instead of N+ implant region 132, transparent gate electrode 534 and N+ source/drain region(s) 536 may form a MOS structure with the MOS channel under transparent gate electrode 534 forming the effective cathode region 532 of the top photodiode 135. The MOS structure formed by transparent gate electrode 534 and N+ source/drain region(s) 536 may have a thinner channel than is possible with an N+ implant layer, thereby potentially allowing depletion region 130 of the top photodiode 135 to form closer to the semiconductor surface 522 than may be possible using the photodetector structure illustrated in FIG. 1A.

To form the cathode region for top photodiode 135, the transparent gate electrode 534 may be biased to produce a very thin (e.g., substantially zero depletion depth) cathode region 532 under the transparent gate electrode. For example, the transparent gate electrode 534 may be biased in the subthreshold region to produce the flat band or zero depletion depth condition. As the bias voltage of the transparent gate electrode 534 relative to the anode (e.g., anode implant regions 542, 544) becomes more positive from the flat band condition, the depletion layer gets deeper until an inversion layer of electrons forms at the surface creating a very thin (e.g., <0.1 µm) conducting layer (illustrated in the short dashed lines of FIG. 5B) substantially similar to the conducting layer of a MOS field effect transistor (FET). For example, the inversion layer may form at the gate threshold voltage of the equivalent MOSFET structure. This thin conducting layer may form the effective cathode region 532 of variable spectral response photodetector 100-c.

If the transparent gate electrode 534 is forward biased further relative to the anode, the depletion layer depth stops growing and the increased charge across the gate capacitor derived from increasing the gate voltage may go entirely into the inversion layer. However, because the thin conducting layer (substantially equivalent to an N+ doping layer) is connected to the N+ source/drain regions 536, the voltage of the N+ source/drain regions 536 and the transparent gate electrode 534 can be increased simultaneously to continue increasing the thickness of the depletion region 130 of the top photodiode 135. By substantially maintaining the voltage difference between the transparent gate electrode 534 and the N+ source/drain regions 536 at approximately the threshold voltage of the MOS cathode structure, the thickness of the depletion region 130 can be increased without substantially increasing the thickness of the cathode depletion region 532 formed by the MOS channel. Therefore, the thickness of the depletion region 130 can be accurately controlled to vary the spectral response of the top photodiode 135. The thickness of the depletion region 150 of the bottom photodiode 155 and the thickness of the common anode region 140 may be controlled using similar techniques to those described above.

Figure 6A:
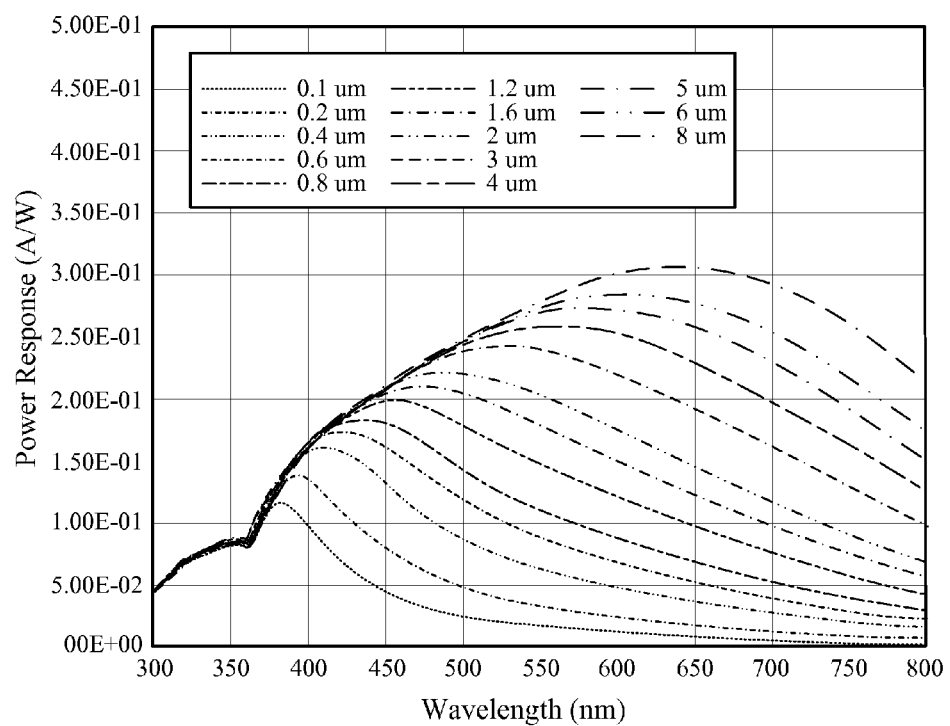
FIG. 6A illustrates example electron photocurrent response curves of a first photodiode of a variable spectral response photodetector at various depletion region thicknesses, according to various embodiments.

FIG. 6A illustrates example electron photocurrent response curves of the top photodiode of variable spectral response photodetector 100 at various collection boundary layer depths, according to various embodiments. In FIG. 6A, the x-axis represents wavelength in nanometers and the y-axis represents an example of photocurrent power response of the top photodiode 135 in amperes per watt of received light.

Figure 6B:
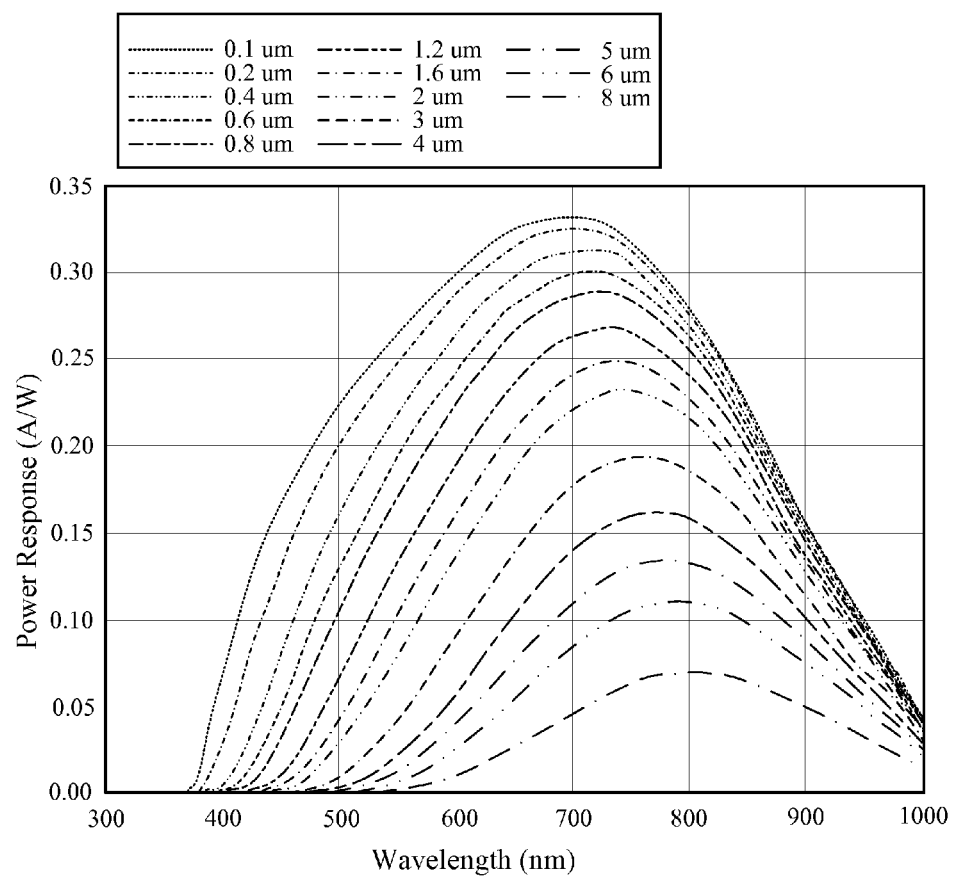
FIG. 6B illustrates example backgate photocurrent response curves of a variable spectral response photodetector at various depletion region thicknesses, according to various embodiments.

FIG. 6B illustrates example photocurrent response curves of the backgate or bottom photodiode 155 at various collection boundary depths, according to various embodiments. In FIG. 6B, the x-axis represents wavelength in nanometers and the y-axis represents an example of photocurrent power response for the bottom photodiode 155 in amperes per watt of received light.

Figure 7:
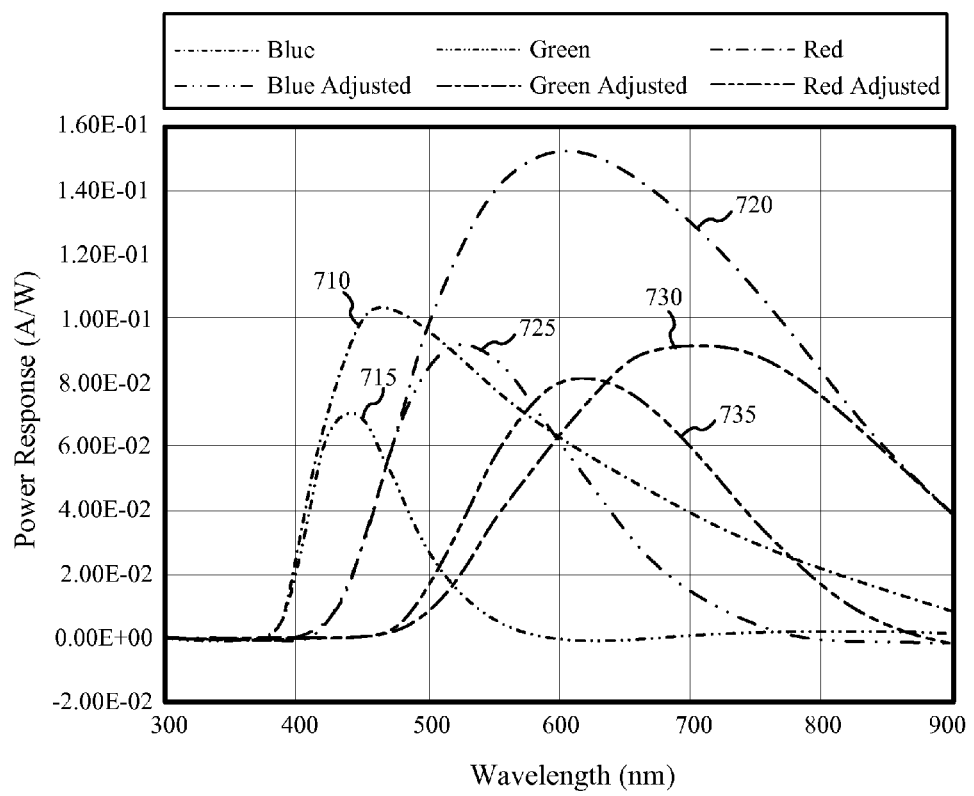
FIG. 7 illustrates an example of using a variable spectral response photodetector to sense light intensity at different wavelength regions.

FIG. 7 illustrates an example of using variable spectral response photodetector 100 to sense light intensity at different wavelength regions. Light intensity for a range of wavelengths (e.g., red, green, blue, UV, infrared, etc.) may be determined by subtracting the measured photocurrent of the top photodiode with the depletion region 130 set at a first thickness from the measured photocurrent of the top photodiode with the depletion region 130 set at a second thickness. For example, according to the photocurrent response of the top photodiode at various thicknesses of depletion region 130 shown in FIG. 7, the blue response 710 may be obtained for incident light by subtracting the measured photocurrent with the depletion region 130 set at a thickness of approximately 0.2 µm from the measured photocurrent with the depletion region 130 set at a thickness of approximately 0.8 µm. The green response 720 may be obtained by subtracting the measured photocurrent with the depletion region 130 set at a thickness of approximately 0.8 µm from the measured photocurrent with the depletion region 130 set at a thickness of approximately 3.5 µm. The red response 730 may be obtained by subtracting the measured photocurrent with the depletion region 130 set at a thickness of approximately 3.0 µm from the measured photocurrent with the depletion region 130 set at a thickness of approximately 5.0 µm.

As can be seen in FIG. 7, response curves obtained by subtracting a first measured photocurrent of the top photodiode at a first thickness from a second measured photocurrent of the top diode at a second thickness may have a substantial response tail in the red and infrared regions. To compensate for the absorbed red and/or infrared light seen in the tail of the response curves, the response curves for the various wavelength ranges may be combined according to a second set of calculations based on measured photocurrent response of the top photodiode or the backgate photodiode.

For example, an adjusted blue response curve 715 may be obtained by subtracting a portion of the unadjusted green response. In the example shown in FIG. 7, 28% of the unadjusted green photocurrent is subtracted to obtain the adjusted blue response 715. An adjusted green response 725 may be obtained by subtracting a portion of the unadjusted red photocurrent. In the example shown in FIG. 7, 150% of the unadjusted red photocurrent is subtracted to obtain the adjusted green response 725. An adjusted red response 735 may be obtained by subtracting a portion of the backgate photocurrent. In the example shown in FIG. 7, 65% of the backgate photocurrent, measured at a thickness of the depletion region 130 of 4.5 µm, is subtracted to obtain the adjusted red response 735. These adjustments are merely examples and other calculations using measured photocurrent of the top photodiode and/or backgate photodiode may be used to obtain other response curves of desired response for a given wavelength range. The portions utilized may be determined by a calibration stage in cooperation with calibrated testing equipment, as is known to those skilled in the art, with the factors stored in memory, or non-volatile storage.

Another example of using variable spectral response photodetector 100 to sense light intensity at different wavelength regions may find use in adapting a light sensor to the human eye response. For example, the visual sensitivity of the human eye has different luminosity functions based on daytime-adapted (photopic) and darkness-adapted (scotopic) conditions. Variable spectral response photodetector 100 may be used to produce light measurements that dynamically account for photopic and scotopic response of the human eye. For example, the techniques described above with reference to FIG. 7 may be used to dynamically adjust the spectral response of variable spectral response photodetector 100 based on the total incident light level.

Figure 8A:
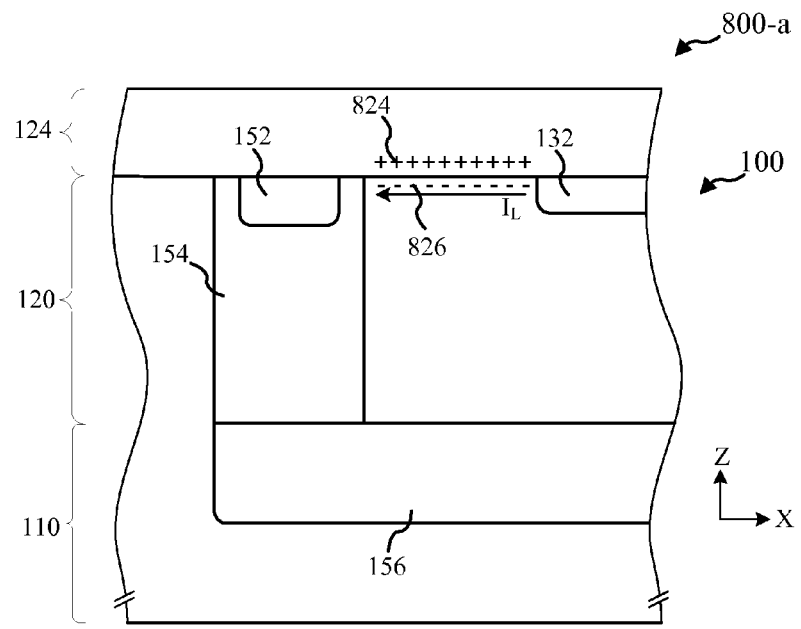
FIG. 8A illustrates a cross section of a variable spectral response photodetector in accordance with various embodiments.

Turning to FIG. 8A, a cross-sectional view 800-*a* of a portion of a variable spectral response photodetector 100 is illustrated in accordance with various embodiments. Cross-sectional view 800-*a* may be, for example, a view of cross-sectional plane $Y_1$-$Y_2$ 174 of variable spectral response photodetector 100-*a* illustrated in FIGS. 1A and 1B. When the reverse bias voltage of the top photodiode 135 is relatively small, charge 824 in an oxide layer 124 near the surface of the photodiode structure may create a parasitic FET that may cause buildup of surface charge 826 which may allow leakage current ($I_L$) between the cathode regions of the top photodiode 135 and the bottom photodiode 155 and/or between the cathode and anode regions of the top photodiode 135 and/or backgate photodiode 155. This leakage current may reduce the accuracy of photocurrent measurements of the top photodiode 135 and/or bottom photodiode 155.

Figure 8B:
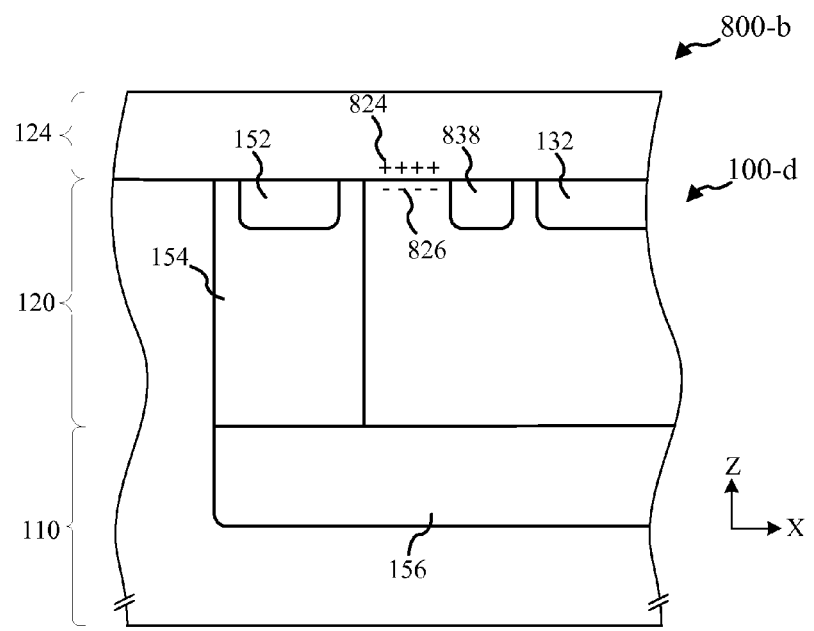
FIG. 8B illustrates a cross section of a variable spectral response photodetector employing an implant region to limit cathode surface leakage current in accordance with various embodiments.

FIG. 8B illustrates a cross-sectional view 800-*b* of a portion of a variable spectral response photodetector 100-*d* employing an implant region to reduce surface cathode leakage in accordance with various embodiments. Variable spectral response photodetector 100-*d* may include an implant region 838 in between the cathode region of the top photodiode 135 (e.g., N+ implant region 132) and the cathode region of the bottom photodiode 155 (e.g., N-well 154). Implant region 838 may be used to increase the surface doping to prevent the natural inversion layer illustrated in FIG. 8A that provides a leakage channel in between the cathode regions of the top photodiode 135 and the bottom photodiode 155. For example, implant region 838 may be a lightly doped P-well region. Implant region 838 may be biased, or, in embodiments, may be unconnected to any bias voltage.

Figure 8C:
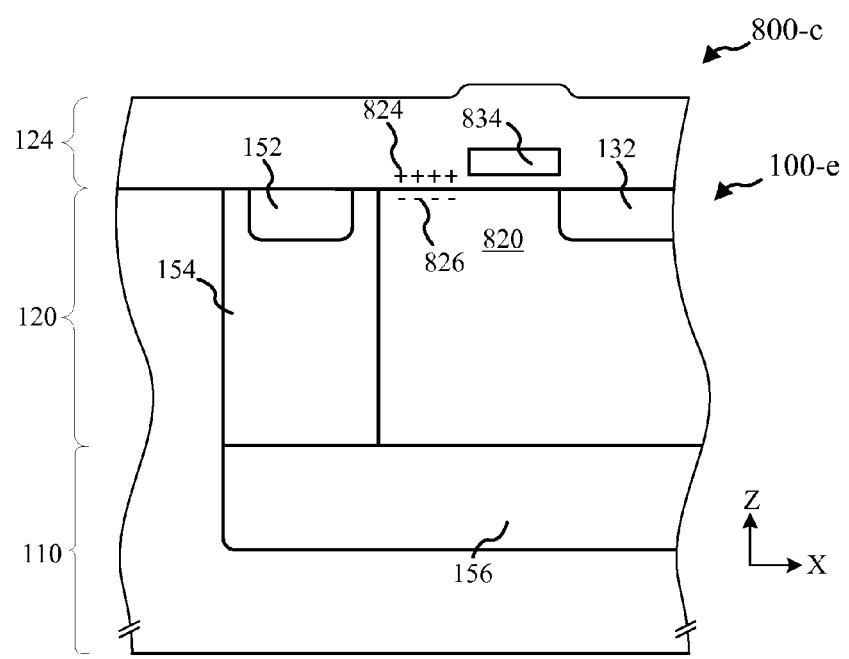
FIG. 8C illustrates a cross section of a variable spectral response photodetector employing an edge gate to limit cathode surface leakage current in accordance with various embodiments.

FIG. 8C illustrates a cross-sectional view 800-*c* of a portion of a variable spectral response photodetector 100-*e* that employs an edge gate to limit surface leakage in accordance with various embodiments. Variable spectral response photodetector 100-*e* may include an edge gate 834 in between the cathode region of the top photodiode 135 (e.g., N+ implant region 132) and the cathode region of the bottom photodiode 155 (e.g., N-well 154). Edge gate 834 may be biased to prevent the formation of an inversion layer under edge gate 834, cutting off the leakage path between the photodiode cathode regions. For example, edge gate 834 may be biased to zero volts, or, in embodiments, negatively biased with respect to the P−epi region 820 by negatively biasing edge gate 834 with respect to the shared cathode of the top photodiode 135 and the bottom photodiode 155 contacted through P+ implant regions 142 and/or 144.

Figure 9:
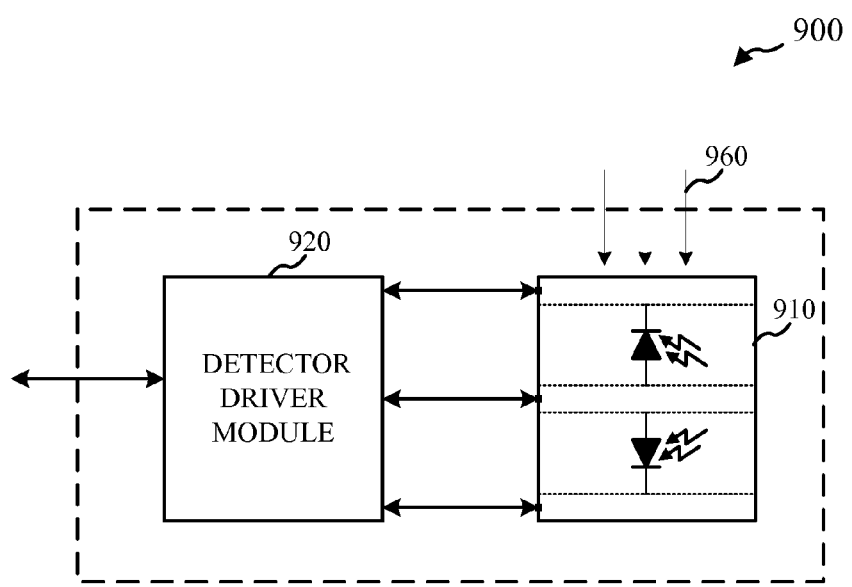
FIG. 9 illustrates a light detector apparatus, according to various embodiments.

FIG. 9 illustrates a light detector apparatus 900, according to various embodiments. Light detector apparatus 900 may include a variable spectral response photodetector 910 that receives incident light 960 and a detector driver module 920 that is coupled to variable spectral response photodetector 910 and controls the spectral response of variable spectral response photodetector 910. Variable spectral response photodetector 910 may be an example of aspects of variable spectral response photodetectors 100 as described above with reference to FIG. 1A, FIG. 1B, FIG. 2A, FIG. 2B, FIG. 2C, FIG. 4A, FIG. 4B, FIG. 5A, FIG. 5B, FIG. 5C, FIG. 8A, FIG. 8B, and/or FIG. 8C. For example, variable spectral response photodetector 910 may include a first photodiode and a second photodiode with a variable depth common anode region.

In embodiments, the first photodiode includes a first depletion region between the light acceptance surface and a common anode region that absorbs a first portion of the incident light. The first photodiode may generate a photocurrent responsive to the absorbed first portion of incident light. The variable spectral response photodetector 910 may include a second photodiode with a second depletion region opposite of the light acceptance surface from the common anode region. The second depletion region may absorb a second portion of the incident light in a second depletion region. The second photodiode may generate a photocurrent responsive to the absorbed second portion of incident light.

Detector driver module 920 may apply bias voltages to the first and second photodiodes of variable spectral response photodetectors 910 to vary the spectral response of photocurrent generated by the photodiodes. Detector driver module 920 may measure photocurrent of the first and/or second photodiodes to determine spectral components of incident light 960. For example, detector driver module 920 may apply a first bias voltage to the first photodiode to set the thickness of the first depletion region to a first predetermined thickness. Detector driver 920 may apply a second bias voltage to the first photodiode to control the thickness of the first depletion region to a second predetermined thickness. Adjusting the thickness of the first depletion region may vary the spectral response of variable spectral response photodetector 910. As described above, adjusting the thickness of the first depletion region, while maintaining a fixed common anode region thickness, may result in an inverse adjustment of the second depletion region.

Detector driver module 920 may make multiple measurements of photocurrent from the first and/or second photodiodes to determine spectral components of the incident light 960. For example, detector driver module 920 may apply multiple voltage bias-points to the first photodiode corresponding to various thicknesses of the first depletion region. The thickness of the common anode region may be controlled by the detector driver module 920 to be substantially the same thickness at each bias-point. The detector driver module 920 may determine spectral components of the incident light for multiple wavelengths and/or wavelength ranges by matrix calculations based on the measured photocurrents and light absorption information as described above.

Figure 10:
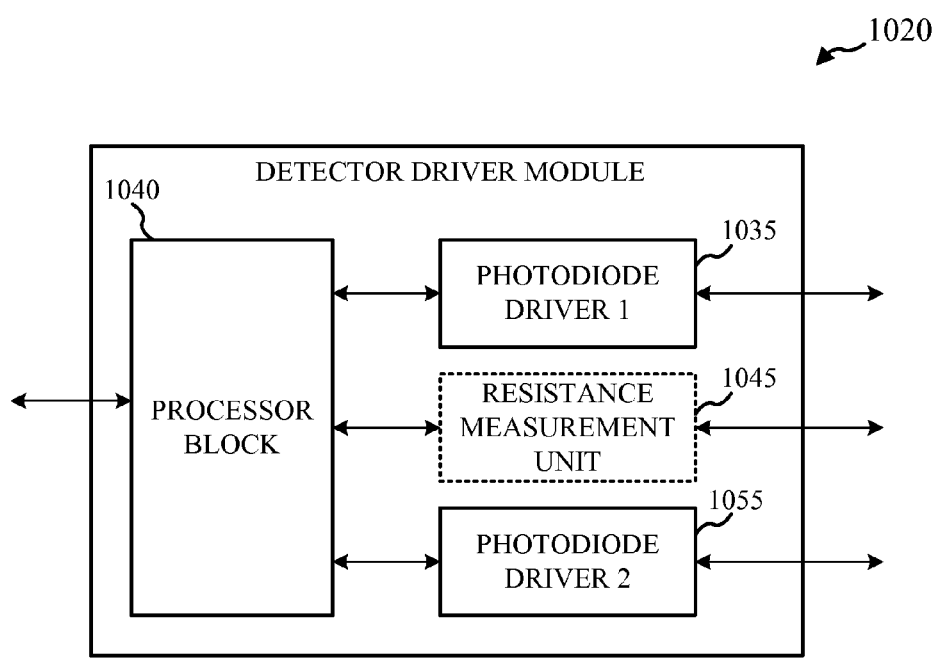
FIG. 10 illustrates a detector driver module for use in a light detector apparatus or system, according to various embodiments.

FIG. 10 illustrates a detector driver module 1020 for use in a light detector apparatus or system, according to various embodiments. Detector driver module 1020 may be an example of one or more aspects of detector driver module 920 described with reference to FIG. 9. Detector driver module 1020 may include a first photodiode driver block 1035, a second photodiode driver block 1055, and/or a processor block 1040. Detector driver module 1020 may include a resistance measurement unit 1045 for measuring resistance of the common anode region of a variable spectral response photodetector. Photodiode driver blocks 1035 and/or 1055 may be operative to apply voltage to photodiodes of a photodetector and measure photocurrent from the photodetector. Photodiode driver blocks 1035 and/or 1055 may include various circuit elements for driving bias voltages to photodiodes and measuring photocurrent from the photodiodes, as is known in the art (e.g., reference voltage generators, amplifiers, transimpedance amplifiers, integrating transimpedance amplifiers, etc.).

Components of detector driver modules 920 and/or 1020, may, individually or collectively, be implemented with one or more Application Specific Integrated Circuits (ASICs) adapted to perform some or all of the applicable functions in hardware. Alternatively, the functions may be performed by one or more other processing units (or cores), on one or more integrated circuits. In other embodiments, other types of integrated circuits may be used (e.g., Structured/Platform ASICs, Field Programmable Gate Arrays (FPGAs), and/or other Semi-Custom ICs), which may be programmed in any manner known in the art. The functions of each unit may also be implemented, in whole or in part, with instructions embodied in a memory, formatted to be executed by one or more general or application-specific processors.

Figure 11:
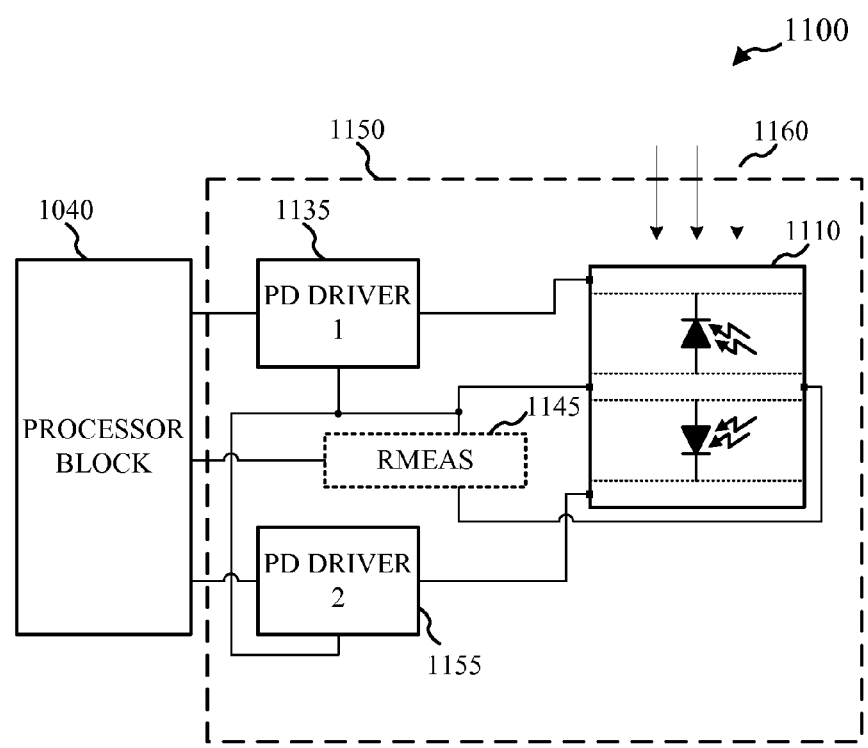
FIG. 11 illustrates a light detector apparatus employing a variable spectral response photodetector, according to various embodiments.

FIG. 11 illustrates a light detector apparatus 1100 employing a variable spectral response photodetector, according to various embodiments. Light detector apparatus 1100 may include a variable spectral response photodetector 1110, a first photodiode driver block 1135, a second photodiode driver block 1155, and/or a processor block 1140. Light detector apparatus 1100 may also include a resistance measurement block 1145 for measuring resistance of a common anode region of the variable spectral response light detector 1110. Variable spectral response photodetector 1110 may be an example of aspects of variable spectral response photodetectors 100 as described above with reference to FIG. 1A, FIG. 1B, FIG. 2A, FIG. 2B, FIG. 2C, FIG. 4A, FIG. 4B, FIG. 5A, FIG. 5B, FIG. 5C, FIG. 8A, FIG. 8B, and/or FIG. 8C. For example, variable spectral response photodetector 1110 may include a first photodiode and a second photodiode with a variable depth collection boundary.

Light detector apparatus 1100 illustrates that various components related to control of variable spectral response photodetector 1110 may be integrated within a single component, integrated circuit substrate, and/or package. In embodiments, variable spectral response light detector 1110, photodiode driver block 1135, and photodiode driver block 1155 are integrated into a single photodetector integrated circuit 1150. The photodetector integrated circuit 1150 may receive digital or analog control signals and output digital or analog representations of measured photocurrent from voltage variable spectral response photodetector 1110. In embodiments, the photodetector integrated circuit 1150 includes resistance measurement block 1145 that measures resistance between electrical contacts of the common anode region of voltage variable spectral response light detector 1110 for operation and/or calibration of the photodetector.

Figure 12:
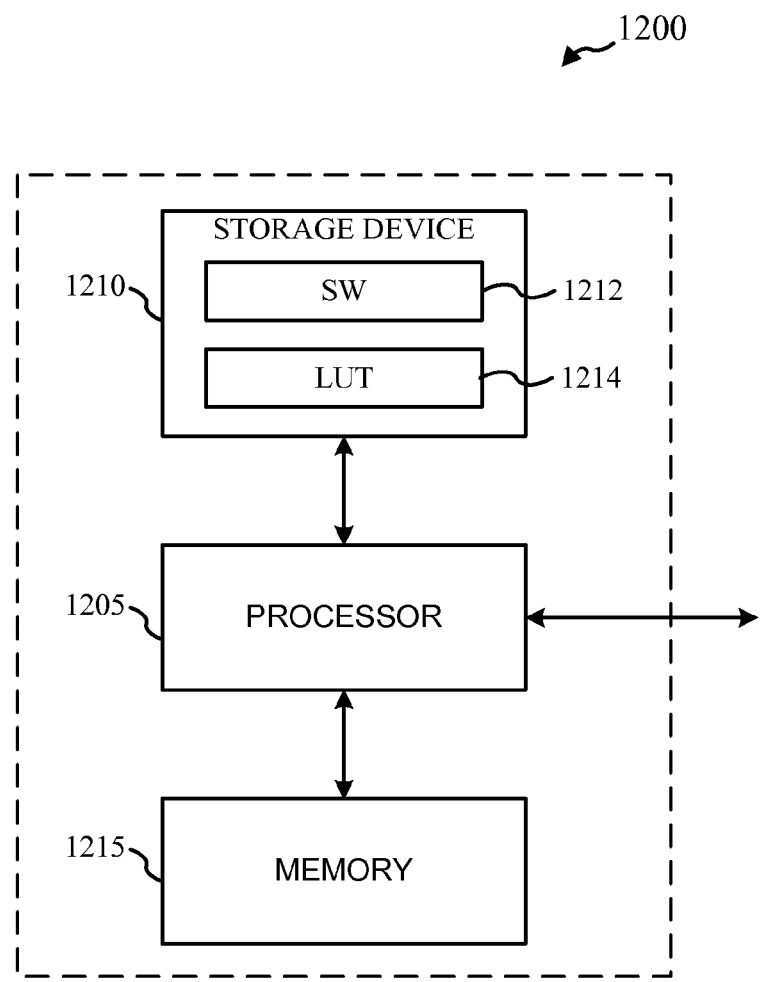
FIG. 12 illustrates a processor block in accordance with various embodiments.

Turning to FIG. 12, a processor block 1200 is illustrated in accordance with various embodiments. Processor block 1200 may include processor 1205, storage device 1210, and/or memory 1215. The processor 1205 may include an intelligent hardware device, e.g., a central processing unit (CPU) such as those made by Intel® Corporation or AMD®, a microcontroller, an application-specific integrated circuit (ASIC), etc. The memory 1215 may include random access memory (RAM) and/or read-only memory (ROM).

The storage device 1210 may include ROM, a solid-state storage device (SSD), a magnetic storage device (hard drive, etc.) and/or the like. The storage device 1210 may also store computer-readable, computer-executable software code 1212 containing instructions that are configured to, when executed, cause the processor 1205 to perform various functions described herein (e.g., setting photodiode bias voltages, measuring photocurrent, etc.). Alternatively, the software code 1212 may not be directly executable by the processor module 1205 but be configured to cause the computer, e.g., when compiled and executed, to perform functions described herein. The storage device 1210 may additionally store information 1214 associated with calibration and/or drive settings for a variable spectral response photodetector. The information 1214 may be stored in an appropriate data structure (e.g., a look-up-table (LUT) and the like) for use by the processor 1205 in setting drive voltages, determining spectral components from measured photocurrent information, and other control functions.

Figure 13:
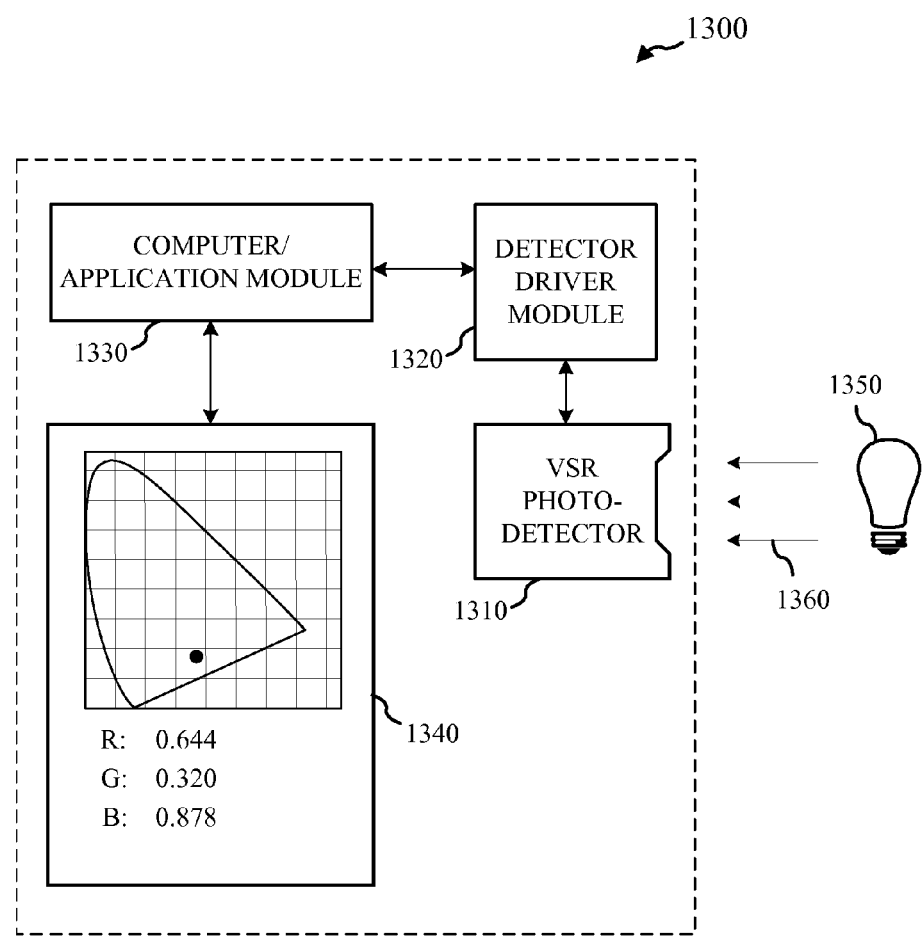
FIG. 13 illustrates a color analyzer system employing a variable spectral response photodetector, according to various embodiments.

FIG. 13 illustrates a color analyzer system 1300 employing a variable spectral response photodetector, according to various embodiments. Color analyzer system 1300 may include variable spectral response photodetector 1310, a detector driver module 1320, a computer or application specific module 1330, and a display screen or user interface 1340. Color analyzer system 1300 may receive incident light 1360 from a light source or object 1350 and be operable to determine one or more spectral components of the incident light 1360. Color analyzer system 1300 may provide graphical or textual output of the spectral components on user interface 1340. Variable spectral response photodetector 1310 may include aspects of variable spectral response light detectors 100 as described above with reference to FIG. 1A, FIG. 1B, FIG. 2A, FIG. 2B, FIG. 2C, FIG. 4A, FIG. 4B, FIG. 5A, FIG. 5B, FIG. 5C, FIG. 8A, FIG. 8B, and/or FIG. 8C. For example, variable spectral response photodetector 1310 may include a first photodiode and a second photodiode with a variable depth common anode region. Detector driver module 1320 may be an example of one or more aspects of detector driver module 920 and/or 1020 described with reference to FIG. 9 and/or FIG. 10.

Computer or application specific module 1330 may be a general purpose computer or application specific computer module that is operable to control higher level functions related to color analyzer system 1300 such as display of information on user interface 1340, calibration of detector driver module 1320 and/or light detector module 1310, storing of spectral component information, etc.

Figure 14:
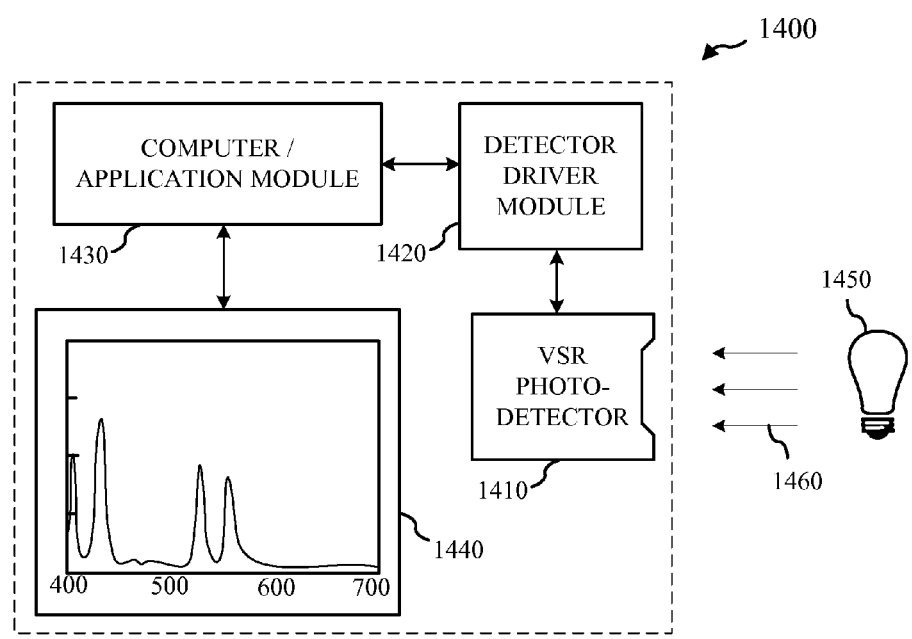
FIG. 14 illustrates a spectrometer system employing a variable spectral response photodetector, according to various embodiments.

FIG. 14 illustrates a spectrometer system 1400 employing a variable spectral response photodetector, according to various embodiments. Spectrometer system 1400 may include variable spectral response photodetector 1410, a detector driver module 1420, a computer or application specific module 1430, and a display screen or user interface 1440. Variable spectral response photodetector 1410 may include aspects of variable spectral response photodetectors 100 as described above with reference to FIG. 1A, FIG. 1B, FIG. 2A, FIG. 2B, FIG. 2C, FIG. 4A, FIG. 4B, FIG. 5A, FIG. 5B, FIG. 5C, FIG. 8A, FIG. 8B, and/or FIG. 8C. For example, variable spectral response photodetector 1410 may include a first photodiode and a second photodiode with a variable depth common anode region. Detector driver module 1420 may be an example of one or more aspects of detector driver module 920 and/or 1020 described with reference to FIG. 9 and/or FIG. 10.

Spectrometer system 1400 may receive incident light 1460 from a light source or object 1450 and be operable to determine spectral components of the incident light 1460 across a range of wavelengths. Spectrometer system 1400 may provide graphical or textual output of the spectral components on user interface 1440. For example, spectrometer system 1400 may scan a wavelength range and graphically illustrate incident light intensity according to wavelength. In embodiments, detector driver module 1420 is operable to apply bias voltages to a first and second photodiode of variable spectral response photodetector 1410 to control spectral response of the variable spectral response photodetector 1410. Detector driver module 1420 may apply predetermined bias voltages to the first and/or second photodiodes and measure photocurrent of the first and/or second photodiodes at multiple voltage bias points. Detector driver module 1420 and/or application module 1430 may determine spectral components of the incident light 1460 at multiple wavelengths or wavelength regions from the measured photocurrent at the multiple voltage bias points. Spectrometer 1400 may be used in spectroscopy applications by passing incident light 1460 through a sample to be analyzed.

Figure 15:
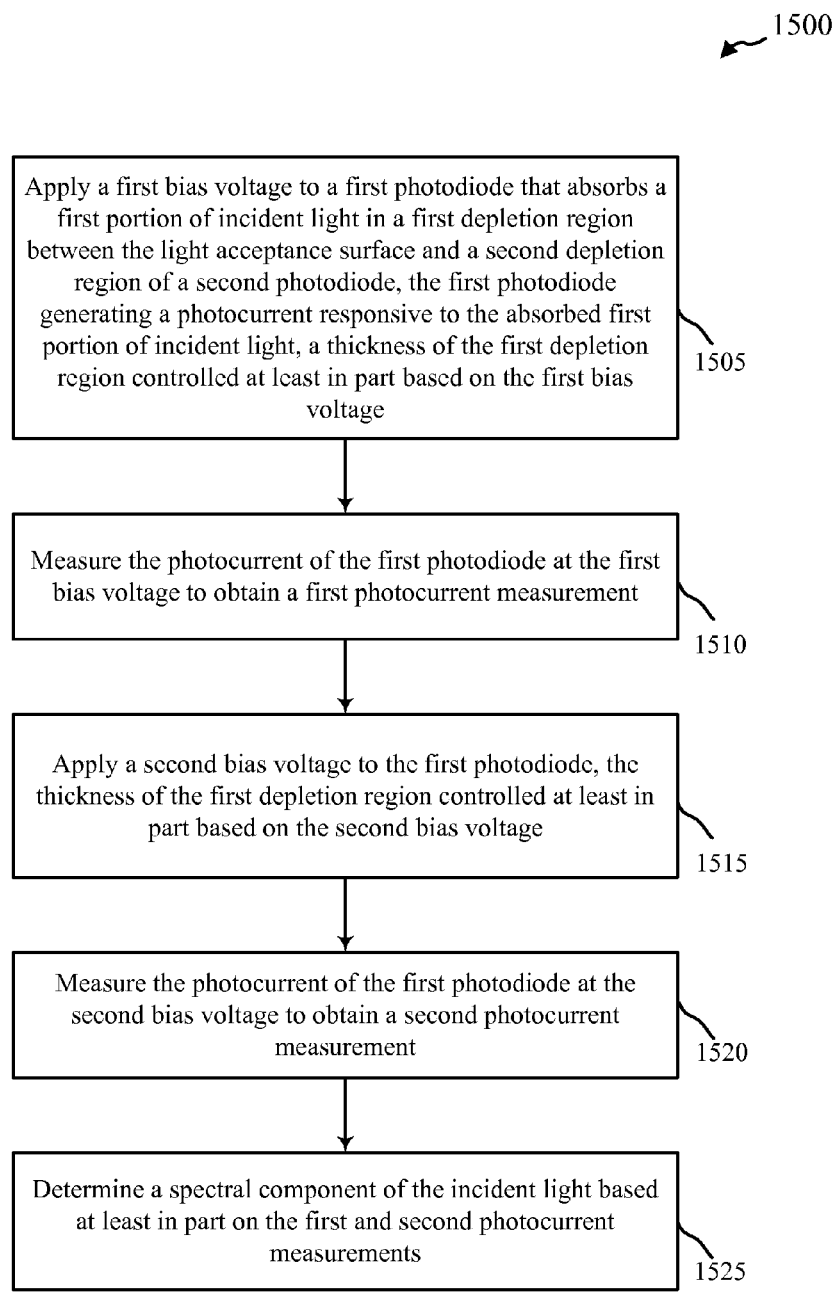
FIG. 15 illustrates a flow diagram of a method for sensing incident light received at a light acceptance surface in accordance with various embodiments.

Turning to FIG. 15, a flow diagram of a method 1500 for sensing incident light received at a light acceptance surface is illustrated in accordance with various embodiments. Method 1500 may be implemented utilizing aspects of light detectors and/or variable spectral response photodetectors including, but not limited to, those illustrated in FIG. 1A, FIG. 1B, FIG. 2A, FIG. 2B, FIG. 2C, FIG. 4A, FIG. 4B, FIG. 5A, FIG. 5B, FIG. 5C, FIG. 8A, FIG. 8B, and/or FIG. 8C.

At block 1505 of method 1500, a first bias voltage may be applied to a first photodiode that absorbs a first portion of incident light in a first depletion region between the light acceptance surface and a second depletion region of a second photodiode, the first photodiode generating a photocurrent responsive to the absorbed first portion of incident light, a thickness of the first depletion region controlled at least in part based on the first bias voltage. The first bias voltage may be selected based on a desired spectral response for sensing incident light. The first bias voltage may be selected based on resistance measurements of the common anode region, capacitance measurements of the first depletion region, and/or calibrated voltage settings determined according to calibration procedures described with reference to FIGS. 2A, 2B, and/or 2C.

At block 1510, the photocurrent of the first photodiode at the first bias voltage may be measured to obtain a first photocurrent measurement. At block 1515, a second bias voltage may be applied to the first photodiode, the thickness of the first depletion region controlled at least in part based on the second bias voltage. The second bias voltage may be selected based on the desired spectral response. The second bias voltage may be selected based on resistance measurements of the common anode region, capacitance measurements of the first depletion region, and/or calibrated voltage settings determined according to calibration procedures described with reference to FIGS. 2A, 2B, and/or 2C.

At block 1520, photocurrent of the first photodiode at the second bias voltage may be measured to obtain a second photocurrent measurement. At block 1525, a spectral component of the incident light may be determined based at least in part on the first photocurrent measurement and the second photocurrent measurement.

Figure 16:
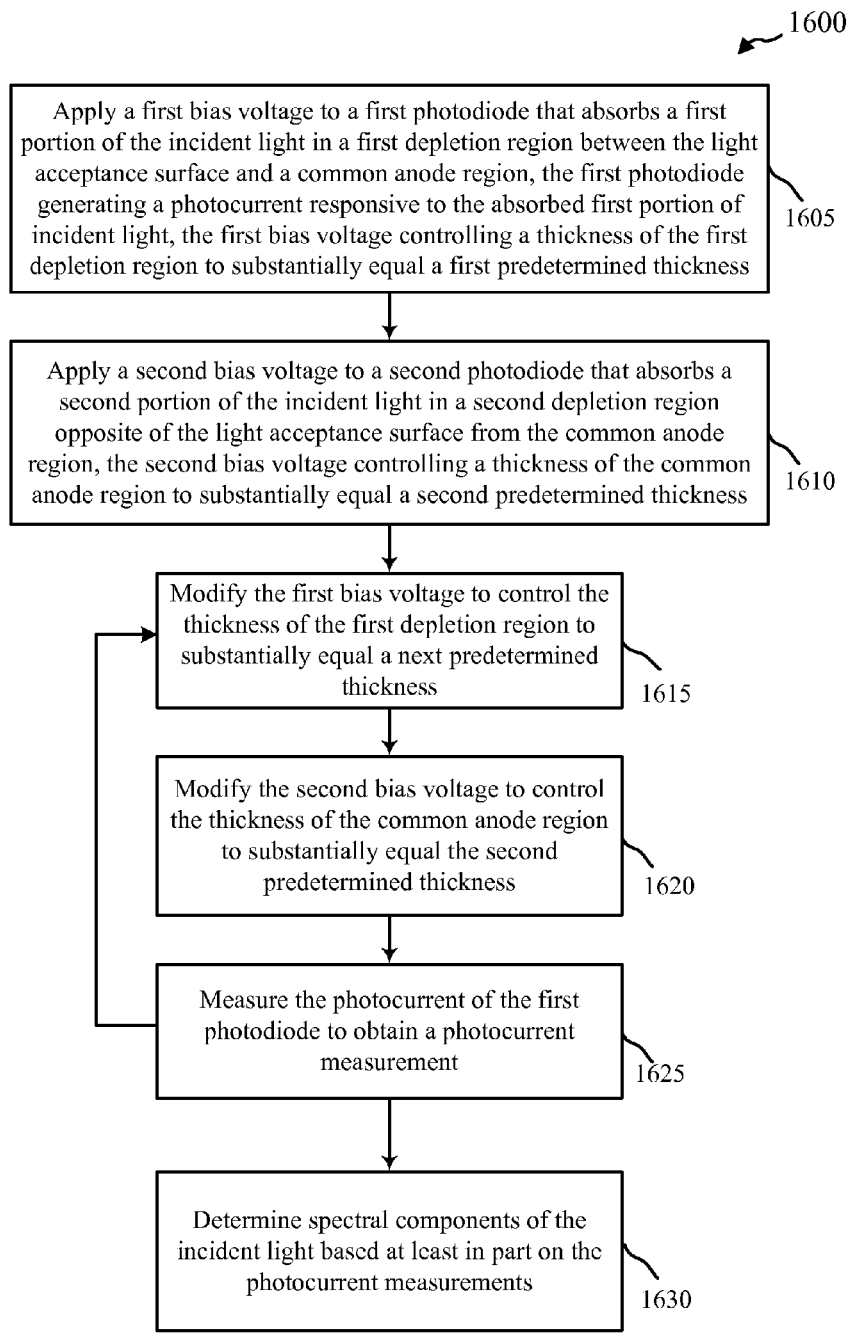
FIG. 16 illustrates a flow diagram of a method for sensing incident light received at a light acceptance surface in accordance with various embodiments.

Turning to FIG. 16, a flow diagram of a method 1600 for sensing incident light received at a light acceptance surface is illustrated in accordance with various embodiments. Method 1600 may be implemented utilizing aspects of light detectors and/or variable spectral response photodetectors 100 including, but not limited to, those illustrated in FIG. 1A, FIG. 1B, FIG. 2A, FIG. 2B, FIG. 2C, FIG. 4A, FIG. 4B, FIG. 5A, FIG. 5B, FIG. 5C, FIG. 8A, FIG. 8B, and/or FIG. 8C.

At block 1605 of method 1600, a first bias voltage may be applied to a first photodiode that absorbs a first portion of the incident light in a first depletion region between the light acceptance surface and a common anode region, the first photodiode generating a photocurrent responsive to the absorbed first portion of incident light, the first bias voltage controlling a thickness of the first depletion region to substantially equal a first predetermined thickness. For example, the first predetermined thickness may be selected based on a desired spectral response for sensing incident light. The first bias voltage may be selected based on resistance measurements of the common anode region, capacitance measurements of the first depletion region, and/or calibrated voltage settings determined according to calibration procedures described with reference to FIGS. 2A, 2B, and/or 2C.

At block 1610, a second bias voltage may be applied to a second photodiode that absorbs a second portion of the incident light in a second depletion region opposite of the light acceptance surface from the common anode region, the second bias voltage controlling a thickness of the common anode region to substantially equal a second predetermined thickness. For example, the second predetermined thickness may correspond to a predetermined thickness of the common anode region used for calibration. The second bias voltage may be selected based on resistance measurements of the common anode region, capacitance measurements of the second depletion region, and/or calibrated voltage settings determined according to calibration procedures described with reference to FIGS. 2A, 2B, and/or 2C.

Blocks 1615, 1620, and 1625 of method 1600 illustrate a process for making multiple photocurrent measurements at multiple bias points of the first bias voltage and the second bias voltage. At block 1615, the first bias voltage is modified to step the thickness of the first depletion region. Modification of the first bias voltage may be performed based on resistance measurements of the common anode region, capacitance measurements of the first depletion region, and/or calibrated voltage settings determined according to calibration procedures described with reference to FIGS. 2A, 2B, and/or 2C. At block 1620, the second bias voltage may be modified to control the thickness of the common anode region to substantially equal the predetermined thickness of stage 1610. At block 1625, photocurrent of the first photodiode is measured to obtain a first photocurrent measurement, and photocurrent of the second photodiode may be measured to obtain a second photocurrent measurement.

At block 1630, spectral components of the incident light are determined based on the photocurrent measurements from repeated iterations of blocks 1615, 1620, and 1625. For example, spectral components at multiple wavelengths or ranges of wavelengths may be determined based on the multiple photocurrent measurements obtained at block 1625. For example, matrix calculation of spectral components may be performed based on the multiple photocurrent measurements and absorption depth information as described in more detail above.

It should be noted that the methods, systems and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted or combined. Also, features described with respect to certain embodiments may be combined in various other embodiments. Different aspects and elements of the embodiments may be combined in a similar manner. Also, it should be emphasized that technology evolves and, thus, many of the elements are exemplary in nature and should not be interpreted to limit the scope of the invention.

Specific details are given in the description to provide a thorough understanding of the embodiments. However, it will be understood by one of ordinary skill in the art that the embodiments may be practiced without these specific details. For example, well-known circuits, processes, algorithms, structures, and techniques have been shown without unnecessary detail in order to avoid obscuring the embodiments.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

Moreover, as disclosed herein, the term "memory" or "memory unit" may represent one or more devices for storing data, including read-only memory (ROM), random access memory (RAM), magnetic RAM, core memory, magnetic disk storage mediums, optical storage mediums, flash memory devices or other computer-readable mediums for storing information. The term "computer-readable medium" includes, but is not limited to, portable or fixed storage devices, optical storage devices, wireless channels, a sim card, other smart cards, and various other mediums capable of storing, containing or carrying instructions or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a computer-readable medium such as a storage medium. Processors may perform the necessary tasks.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

What is claimed is:

1. An apparatus for sensing incident light, the apparatus comprising:
   a light detector that receives the incident light at a light acceptance surface, comprising:
      a first photodiode that absorbs a first portion of the incident light in a first depletion region, the first photodiode generating a photocurrent responsive to the absorbed first portion of incident light; and
      a second photodiode that absorbs a second portion of the incident light in a second depletion region, the first depletion region between the second depletion region and the light acceptance surface; and
   a detector driver module coupled with the light detector, the detector driver module configured to:
      apply a first bias voltage to the first photodiode, a thickness of the first depletion region controlled at least in part based on the first bias voltage;
      apply a second bias voltage to the first photodiode different than the first bias voltage, the thickness of the first depletion region controlled at least in part based on the second bias voltage;
      measure the photocurrent of the first photodiode at each of the first and second bias voltages to obtain at least two photocurrent measurements; and
      determine a spectral component of the incident light based at least in part on the at least two photocurrent measurements.

2. The apparatus of claim 1, the detector driver module further configured to:
   apply a third bias voltage to the second photodiode while applying the first bias voltage to the first photodiode, the thickness of the second depletion region controlled at least in part based on the third bias voltage;
   measure the photocurrent of the second photodiode at the third bias voltage;
   apply a fourth bias voltage to the second photodiode while applying the second bias voltage to the first photodiode, the fourth bias voltage different from the third bias voltage, the thickness of the second depletion region controlled at least in part based on the fourth bias voltage; and
   determine the spectral component of the incident light further based at least in part on the photocurrent measurements at the third and fourth bias voltages.

3. The apparatus of claim 2, wherein the third and fourth bias voltages are selected such that a thickness of a common anode region between the first depletion region and the second depletion region is substantially the same when the first and second bias voltages are applied.

4. The apparatus of claim 3, wherein the thickness of the common anode region is controlled at least in part responsive to a resistance of the common anode region.

5. The apparatus of claim 1, wherein the detector driver module is configured to control the thickness of the first depletion region at each of the first and second bias voltages based at least in part on a capacitance of the first depletion region.

6. The apparatus of claim 1, wherein the detector driver module is configured to:
   measure a photocurrent of the second photodiode responsive to the absorbed second portion of the incident light at one or more of the first and second bias voltages to obtain one or more backgate photocurrent measurements; and
   determine a second spectral component of the incident light based at least in part on the at least two photocurrent measurements and the one or more backgate photocurrent measurements.

7. The apparatus of claim 1, wherein the detector driver module comprises:
   a first voltage control module coupled with the first photodiode;
   a first current measurement module coupled with the first photodiode; and
   a processor module coupled with the first voltage control module and the first current measurement module, the processor module configured to determine the spectral component of the incident light based at least in part on the at least two photocurrent measurements via the first current measurement module and light absorption depth information.

8. The apparatus of claim 6, wherein the detector driver module further comprises:
   a second voltage control module coupled with the second photodiode; and
   a second current measurement module coupled with the second photodiode,
   wherein the processor module is further coupled with the second voltage control module and the second current measurement module, the processor module further configured to determine the spectral component of the incident light based at least in part on photocurrent measurements via the second current measurement module at each of the first and second bias voltages.

9. A method for sensing incident light received at a light acceptance surface, the method comprising:
   applying a first bias voltage to a first photodiode that absorbs a first portion of the incident light in a first depletion region between the light acceptance surface and a second depletion region of a second photodiode, the first photodiode generating a photocurrent responsive to the absorbed first portion of incident light, a thickness of the first depletion region controlled at least in part based on the first bias voltage;

measuring the photocurrent of the first photodiode at the first bias voltage to obtain a first photocurrent measurement;

applying a second bias voltage different than the first bias voltage to the first photodiode, the thickness of the first depletion region controlled at least in part based on the second bias voltage;

measuring the photocurrent of the first photodiode at the second bias voltage to obtain a second photocurrent measurement;

determining a spectral component of the incident light based at least in part on the first photocurrent measurement and the second photocurrent measurement.

10. The method of claim 9, further comprising:

applying a third bias voltage to the second photodiode while applying the first bias voltage to the first photodiode, a thickness of the second depletion region controlled at least in part based on the third bias voltage;

measuring the photocurrent of the second photodiode at the third bias voltage to obtain a third photocurrent measurement;

applying a fourth bias voltage to the second photodiode while applying the second bias voltage to the first photodiode, the fourth bias voltage different from the third bias voltage, the thickness of the second depletion region controlled at least in part based on the fourth bias voltage; and determining the spectral component of the incident light further based at least in part on the third photocurrent measurement and the fourth photocurrent measurement.

11. The method of claim 9, wherein the applying the third and fourth bias voltages comprises:

controlling a thickness of a common anode region between the first depletion region and the second depletion region to be substantially equal when the first and second bias voltages are applied.

12. The method of claim 11, wherein the thickness of the common anode region is controlled at least in part responsive to a resistance of the common anode region.

13. The method of claim 9, wherein the applying the first and second bias voltages comprises:

controlling the thickness of the first depletion region at each of the first and second bias voltages based at least in part on a capacitance of the first depletion region.

14. The method of claim 10, wherein the applying the third and fourth bias voltages comprises:

controlling the thickness of the second depletion region at each of the third and fourth bias voltages based at least in part on a capacitance of the second depletion region.

15. The method of claim 9, further comprising:

measuring photocurrent at a first plurality of bias points by iteratively:
stepping the thickness of the first depletion region by a predetermined step thickness by, at least in part, modifying the second bias voltage; and
measuring the photocurrent of the first photodiode; and
determining an amount of received light at a second plurality of wavelength ranges by solving a matrix calculation based at least in part on the measured photocurrent at the first plurality of bias points and light absorption depth information.

16. The method of claim 15, wherein a number of photocurrent measurements measured at the first plurality of bias points is greater than a number of wavelength ranges of the second plurality of wavelength regions.

17. The method of claim 15, further comprising:

adjusting the matrix calculation to adjust a calculated spectral response based at least in part on a metric of the measured photocurrent at one or more bias points.

18. The method of claim 17, wherein the metric of the measured photocurrent comprises a combined incident light level.

* * * * *